(12) United States Patent
Diamond et al.

(10) Patent No.: US 9,910,048 B2
(45) Date of Patent: Mar. 6, 2018

(54) METHOD FOR DETECTION OF AGGREGATES IN BIOLOGICAL SAMPLES

(71) Applicant: Washington University, St. Louis, MO (US)

(72) Inventors: Marc Diamond, St. Louis, MO (US); Najla Kfoury, St. Louis, MO (US); Brandon B. Holmes, St. Louis, MO (US); Jennifer L. Furman, St. Louis, MO (US)

(73) Assignee: WASHINGTON UNIVERSITY, Saint Louis, MO (US)

( * ) Notice: Subject to any disclaimer, the term of this patent is extended or adjusted under 35 U.S.C. 154(b) by 159 days.

(21) Appl. No.: 14/649,440

(22) PCT Filed: Dec. 3, 2013

(86) PCT No.: PCT/US2013/072905
§ 371 (c)(1),
(2) Date: Jun. 3, 2015

(87) PCT Pub. No.: WO2014/089104
PCT Pub. Date: Jun. 12, 2014

(65) Prior Publication Data
US 2015/0309054 A1    Oct. 29, 2015

Related U.S. Application Data

(60) Provisional application No. 61/732,658, filed on Dec. 3, 2012, provisional application No. 61/784,178, filed on Mar. 14, 2013.

(51) Int. Cl.
*G01N 33/68* (2006.01)
*G01N 33/50* (2006.01)

(52) U.S. Cl.
CPC ..... *G01N 33/6896* (2013.01); *G01N 33/5008* (2013.01); *G01N 2333/4703* (2013.01); *G01N 2800/2821* (2013.01); *G01N 2800/2835* (2013.01)

(58) Field of Classification Search
None
See application file for complete search history.

(56) References Cited

U.S. PATENT DOCUMENTS 7,803,559 B1    9/2010   Diamond et al.
2008/0003604 A1 1/2008   Ruff et al.

FOREIGN PATENT DOCUMENTS

WO    2006033974 A2    3/2006

OTHER PUBLICATIONS

Merrill, Ronald A; Strack, Stefan; "Protein Kinases and Phosphatases" Molecular Pain, Chapter 15, 187-205, 2007.*
Kfoury, et al.; Trans-cellular propagation of Tau aggregation by fibrillar species; J. Biol. Chem.; 2012; pp. 19440-19451, vol. 287, No. 23.
Rajan, et al.; Specificity in intracellular protein aggregation and inclusion body formation; PNAS; 2001; pp. 13060-13065, vol. 98, No. 23.
International Preliminary Report on Patentability for related PCT Application No. PCT/US2013/072905.

* cited by examiner

*Primary Examiner* — David W Berke-Schlessel
(74) *Attorney, Agent, or Firm* — Polsinelli PC

(57) ABSTRACT

The present invention provides a method for detecting protein aggregates in a biological sample, and uses thereof.

5 Claims, 20 Drawing Sheets
(6 of 20 Drawing Sheet(s) Filed in Color)

US 9,910,048 B2

METHOD FOR DETECTION OF AGGREGATES IN BIOLOGICAL SAMPLES

CROSS REFERENCE TO RELATED APPLICATIONS

This application claims the priority of U.S. provisional application No. 61/732,658, filed Dec. 3, 2012 and U.S. provisional application No. 61/784,178, filed Mar. 14, 2013, each of which is hereby incorporated by reference in its entirety.

GOVERNMENTAL RIGHTS

This invention was made with government support under NS071835 and NS079039 awarded by the National Institutes of Health. The government has certain rights in the invention.

FIELD OF THE INVENTION

The present invention encompasses methods for detecting aggregates in biological samples using a cell-based assay.

BACKGROUND OF THE INVENTION

High-throughput assays to measure intracellular protein aggregation using fluorescence resonance energy transfer (FRET) are known in the art, and have been successfully used to screen for inhibitors of aggregation. For instance, U.S. Pat. No. 7,803,559 teaches a high-throughput assay to measure intracellular polyglutamine protein aggregation using FRET. Similar assays designed to measure intracellular tau aggregation have also been described. For example, see Kfoury et al. (J Biol Chem 2012). While these methods are capable of detecting recombinant protein, the lower limit of detection for these assays precludes their usefulness with biological samples such as blood and CSF, where the concentration of the protein aggregate "seed" is orders of magnitude lower. Hence, there is a need in the art for a method to detect protein aggregates in biological samples.

SUMMARY OF THE INVENTION

In an aspect, the present invention provides a method for detecting one or more protein aggregates in a biological sample. The method comprises the steps of: (a) providing at least one mammalian cell comprising a first protein linked to a first reporter and a second protein linked to a second reporter, wherein the first protein and the second protein each comprise a similar aggregation-prone domain, such that the first protein and the second protein aggregate and produce a detectable signal; (b) contacting the at least one mammalian cell with a biological sample comprising a protein aggregate at a concentration equivalent to about 1 pm to about 100 nM of monomers, the protein aggregate comprising an aggregation-prone domain similar to the first and second protein, such that the protein aggregate is taken up by the cell; (c) measuring a detectable signal; and (d) comparing the amount of the detectable signal in the biological sample to the amount of a detectable signal produced by a control, wherein a change in the detectable signal indicates one or more protein aggregates are in the biological sample. In certain embodiments, the detectable signal is measured by flow cytometry. In certain embodiments, the mammalian cell stably expresses first protein linked to a first reporter and a second protein linked to a second reporter. In certain embodiments, the mammalian cell transiently expresses the first protein linked to the first reporter and the second protein linked to the second reporter.

Other aspects and iterations of the invention are described more thoroughly below.

BRIEF DESCRIPTION OF THE FIGURES

The application file contains at least one photograph executed in color. Copies of this patent application publication with color photographs will be provided by the Office upon request and payment of the necessary fee.

DETAILED DESCRIPTION OF THE INVENTION

Figure 1:
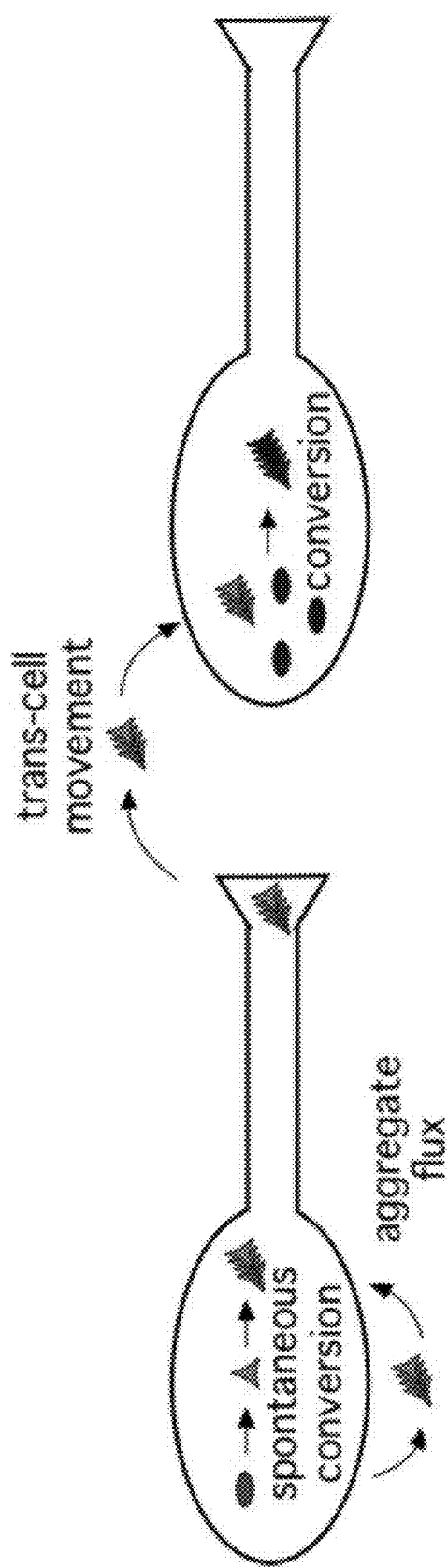
FIG. 1 is an illustration depicting propagation of aggregate pathology by aggregate transfer. Multiple lines of work now indicate that aggregate flux between cells can account for spread of neuropathology in neurodegenerative diseases. Briefly, misfolding of an aggregation-prone protein occurs due to an unknown discrete event or spontaneously (left cell, conversion of red oval to red triangle), leading to intracellular formation of protein aggregate (left cell, accumulation of red triangles). Protein aggregate in a donor cell (red triangles) can then escape the cell, enter a recipient cell (right), and directly contact natively folded protein (right cell, blue ovals) to amplify the misfolded state (right cell, blue triangles). This cell-cell movement is mediated by aggregates (e.g. fibrils) that are released directly into the medium.

The present invention provides a method to detect protein aggregates in a biological sample. Methods to detect protein aggregation known in the art were designed to screen and identify inhibitors of protein aggregation, but are not suited to detect protein aggregates at concentrations that may be physiologically relevant, albeit very low. Using the method of the invention, it is now possible to detect these protein aggregates in biological samples, such as brain lysates. Importantly, through the use of these methods with peripheral tissues, such as CSF and plasma, it may be possible to diagnose and monitor diseases where pathological protein aggregation plays a role.

I. METHOD FOR DETECTING ONE OR MORE PROTEIN AGGREGATES IN A BIOLOGICAL SAMPLE

In one aspect, a method of the invention provides means to detect and quantify one or more protein aggregates in a biological sample. Typically, the method comprises (a) providing at least one mammalian cell comprising a first protein linked to a first reporter and a second protein linked to a second reporter, wherein the first protein and the second protein each comprise a similar aggregation-prone domain, such that the first protein and the second protein aggregate and produce a detectable signal; (b) contacting the at least one mammalian cell with a biological sample comprising a protein aggregate at a concentration equivalent to about 1 pM to about 100 nM of monomers, the protein aggregate comprising an aggregation-prone domain similar to the first and second protein, such that the protein aggregate is taken up by the cell; (c) measuring a detectable signal; and (d) comparing the amount of the detectable signal in the biological sample to the amount of a detectable signal produced by a control, wherein a change in the detectable signal indicates one or more protein aggregates are in the biological sample. Each aspect of the method is described in more detail below.

A. Protein Aggregate

Suitable protein aggregates may be comprised of any protein with an aggregation-prone domain. The term "protein", as used herein, includes peptides, polypeptides, fusion proteins, naturally occurring proteins, recombinant or artificially synthesized proteins, and analogs, fragments, derivatives or combinations thereof. The term "aggregation-prone domain" refers to a region of the amino acid sequence of a protein that promotes the protein's aggregation. For example, the tau protein has either three or four repeat regions that constitute the aggregation-prone core of the protein, which is often termed the repeat domain (RD). Expression of the tau RD causes pathology in transgenic mice, and it reliably forms fibrils in cultured cells. As another example, the androgen receptor (AR) and huntingtin (htt) have expanded tracts of glutamines that contribute to formation of perinuclear and nuclear aggregates of these proteins. In some embodiments, an aggregation-prone domain is unique to a single protein. In other embodiments, an aggregation prone domain may be common to more than one protein. Aggregation-prone domains are well known in the art, or may be predicted through computational modeling.

A protein aggregate may be comprised of recombinant or naturally occurring protein, or a combination thereof. In some embodiments, a protein aggregate is comprised of recombinant protein. As used herein, "recombinant protein" refers to a protein that is encoded by a nucleic acid sequence that is not typically present in the wild-type genome of the cell expressing it. Methods of making and expressing recombinant protein are well known in the art. In other embodiments, a protein aggregate is comprised of naturally occurring protein. As used herein, "naturally occurring protein" refers to a protein that is encoded by a nucleic acid sequence that is typically present in the wild-type genome of the cell expressing it. In still other embodiments, a protein aggregate is comprised of a combination of recombinant and naturally occurring protein.

The amount of protein in a protein aggregate and the total number or protein aggregates in a sample can and will vary. Generally, a protein aggregate is comprised of two or more proteins. For example, a protein aggregate may be comprised of at least 2, at least 3, at least 4, at least 5, at least 6, at least 7, at least 8, at least 9, at least 10, at least 15, at least 16, at least 17, at least 18, at least 19, or at least 20 proteins. In another example, a protein aggregate may be comprised of at least 25, at least 30, at least 35, at least 40, at least 45, at least 50, at least 55, at least 60, at least 65, at least 70, at least 75, at least 80, at least 85, at least 90, at least 95, or at least 100 proteins. The precise amount of protein in each aggregate is difficult to measure, as this would require separation and isolation of a single aggregate from the sample. Therefore, the amount of protein in any aggregate in a sample is expressed as the equivalent concentration of monomers. As used herein, the terms "equivalent concentration of monomers" and "monomer-equivalents" are used interchangeably. For example, if a sample contains one protein aggregate consisting of two tau proteins forming the aggregate, the protein concentration in the sample is equivalent to two individual tau monomers, or two monomer-equivalents of tau. In another example, if a sample contains two of the protein aggregates described in the first example, then the protein concentration in the sample is four monomer-equivalents of tau.

Methods of making a protein aggregate are well known in the art. Generally, a protein aggregate may form when two or more of the same aggregation-prone domains from different proteins interact. A protein aggregate may form in the presence of a cell, either intracellularly or extracellularly, or in the absence of a cell. Said another way, a cell may produce protein with an aggregation-prone domain and the proteins may interact inside the cell or, if secreted, outside the cell to form a protein aggregate. Alternately, aggregate formation may be induced by "seeds". As used herein, "seed" refers to one or more proteins that nucleate aggregation of other proteins with a similar aggregation domain. A seed may be purified protein that aggregates at a critical concentration or induces aggregation when added to a culture of cells producing a protein with the same aggregation domain. A seed, however, need not be in a purified form to induce aggregation. For example, a seed may also be protein aggregate released from a cell, as recently described by Kfoury et al. (J Biol Chem 2012), and, therefore, a biological sample or conditioned cell medium comprising the seed may induce protein aggregation. Methods of making a protein aggregate to be measured by the method of the invention, including seeds and biological samples comprising seeds, are further detailed in Kfoury et al. (J Biol Chem 2012) and the Examples. Suitable biological samples are described in further detail below.

In exemplary embodiments, a protein aggregate is comprised of a pathological protein. The term "pathological protein", as used herein, refers to a protein that aggregates, whereby aggregation is closely linked to disease pathology. Pathological proteins are well-known in the art. A pathological protein may be a polyglutamine expansion protein or a non-polyglutamine expansion protein. Polyglutamine expansion diseases are a class of neurodegenerative diseases associated with pathological aggregation of a protein containing expanded tracts of glutamines (e.g. a polyglutamine expansion protein). Pathological polyglutamine expansion proteins (and their related disorders) may include, but are not limited to, htt (Huntington's disease), androgen receptor (AR; spinobulbar muscular atrophy), ATN1 (dentatorubro-pallidoluysian atrophy), ATXN1 (Spinocerebellar ataxia Type 1), ATXN2, (Spinocerebellar ataxia Type 2), ATXN3, (Spinocerebellar ataxia Type 3), CACNA1A (Spinocerebellar ataxia Type 6), ATXN7 (Spinocerebellar ataxia Type 7), and TBP (Spinocerebellar ataxia Type 17). Non-limiting examples of non-polyglutamine expansion proteins include tau, synuclein, superoxide dismutase (SOD1), PABPN1, amyloid beta, serpin, transthyretin, TDP-43 (TARDBP), valosin containing peptide (VCP), hnRNPA2B1 and hnRNPA1 and prion protein. Tauopathies are another class of neurodegenerative diseases associated with the pathological aggregation of tau protein into fibrillar tau aggregates. Exemplary disorders that have symptoms associated with tau aggregation include, but are not limited to, progressive supranuclear palsy, dementia pugilistica (chronic traumatic encephalopathy), frontotemporal dementia and parkinsonism linked to chromosome 17, Lytico-Bodig disease (Parkinson-dementia complex of Guam), tangle-predominant dementia, ganglioglioma and gangliocytoma, meningioangiomatosis, subacute sclerosing panencephalitis, lead encephalopathy, tuberous sclerosis, Hallervorden-Spatz disease, lipofuscinosis, Pick's disease, corticobasal degeneration, argyrophilic grain disease (AGD), Frontotemporal lobar degeneration, Alzheimer's Disease, and frontotemporal dementia. Exemplary disorders that have symptoms associated with SOD1 aggregation may include amyotrophic lateral sclerosis (Lou Gehrig's disease). Exemplary disorders that have symptoms associated with PABPN1 aggregation may include oculopharyngeal muscular dystrophy. Exemplary disorders that have symptoms associated with synuclein aggregation may include Parkinson's disease, Alzheimer's disease, Lewy body disease and other neurodegenerative diseases. Exemplary disorders that have symptoms associated with serpin aggregation ("serpinopathies") may include alpha 1-antitrypsin deficiency which may cause familial emphysema and liver cirrhosis, certain familial forms of thrombosis related to antithrombin deficiency, types 1 and 2 hereditary angioedema related to deficiency of C1-inhibitor, and familial encephalopathy with neuroserpin inclusion bodies. Exemplary disorders that have symptoms associated with transthyretin aggregation may include senile systemic amyloidosis, familial amyloid polyneuropathy, and familial amyloid cardiomyopathy. Exemplary disorders that have symptoms associated with prion aggregation may include scrapie, bovine spongiform encephalopathy (mad cow disease), transmissible mink encephalopathy, chronic wasting disease, feline spongiform encephalopathy, exotic ungulate encephalopathy, Creutzfeldt-Jakob diseases, Gerstmann-Straussler-Scheinker syndrome, fatal familial insomnia, and Kuru. Exemplary disorders that have symptoms associated with TDP-43 aggregation may include FTLD-TDP and chronic traumatic encephalopathy. Exemplary disorders that have symptoms associated with amyloid beta aggregation may include Alzheimer's disease, Lewy body disease, cerebral amyloid angiopathy, inclusion body myositis and traumatic brain injury. Exemplary conditions that are associated with VCP aggregation include Inclusion body myopathy with early-onset Paget disease and frontotemporal dementia (IBMPFD). Exemplary conditions caused by hnRNPA2B1 and hnRNPA1 include multisystem proteinopathy and ALS.

In a preferred embodiment, a protein aggregate is comprised of tau. In another preferred embodiment, a protein aggregate is comprised of AR. In still another preferred embodiment, a protein aggregate is comprised of htt. In yet another preferred embodiment, a protein aggregate is comprised of TDP-43. In a different preferred embodiment, a protein aggregate is comprised of amyloid beta. In an alternative preferred embodiment, a protein aggregate is comprised of prion protein. In another preferred embodiment, a protein aggregate is comprised of α-synuclein.

B. Eukaryotic Cell-Based Assay

In another aspect, a method of the invention encompasses a cell-based assay to detect and quantify protein aggregation. Generally speaking, the cell-based assay comprises at least one eukaryotic cell comprising a first protein linked to a first reporter and a second protein linked to a second reporter, wherein the first protein and the second protein aggregate producing a detectable signal. Said another way, the first and second protein, each a recombinant protein linked to a unique reporter, act together as an intracellular "biosensor" that produces a detectable signal when the first and second protein are aggregated. Advantageously, the amount of detectable signal produced by a eukaryotic cell-based assay of the invention is responsive to intracellular and extracellular protein aggregates. Suitable examples of a cell-based system of the invention are described in detail in U.S. Pat. No. 7,803,559 and Kfoury et al. (J Biol Chem 2012), both of which are incorporated herein by reference in their entirety, as well as in the Examples. The terms "cell-based assay", "biosensor cell line", and "biosensor system" may be used interchangeably, and refer to the cell-based assay of the invention comprising at least one eukaryotic cell comprising a first protein linked to a first reporter and a second protein linked to a second reporter, wherein the first protein and the second protein aggregate producing a detectable signal.

(i) Eukaryotic Cell

Any eukaryotic cell known in the art that may be cultured in vitro and can take up a protein or protein aggregate of the invention is suitable for the method of the invention. As used herein, the term "take up" refers to the movement of a protein or protein aggregate from the outside of the cell to the inside of the cell, whether the process is actively mediated by the cell (for example, endocytosis) or occurs passively (for example, facilitated diffusion).

A eukaryotic cell may or may not be a mammalian cell. In some embodiments, a eukaryotic cell is an insect cell. Non-limiting examples of suitable insect cell may include *Drosophila* cells, *Lepidoptera* or *Spodoptera* cells, or *Trichoplusia ni* embryonic tissue cells. Suitable *Drosophila* cells may, include, but are not limited to S2 cells. Suitable *Lepidoptera* or *Spodeptera* cells may, include, but are not limited to Sf9, Sf21, and mimic-Sf9 cells. Suitable *Trichoplusia ni* embryonic tissue cells may, include, but are not limited to Tn5Bl-4 (High Fives) and Tn268 cells. In other embodiments, a eukaryotic cell is a yeast cell. In preferred embodiments, a eukaryotic cell is a mammalian cell.

A mammalian cell may be a human cell or a non-human cell. In some embodiments, a mammalian cell is a human cell. Non-limiting examples of human cells may include HEK293 cells and primary neural cells. In other embodiments, a mammalian cell is a non-human cell. Non-limiting examples of non-human cells may include COS-7, C17.2 neural precursor cells, PC-12 cells and primary neural cells from non-human mammals. In exemplary embodiments, a mammalian cell is a HEK293 cell.

Methods of culturing eukaryotic cells in vitro are well known to one of skill in the art and can be found in a variety of references including, e.g., Basic Cell Culture: A Practical Approach. J. Davis, Oxford University Press (2002) 416 pp. 2nd edition. Similarly, methods of making a eukaryotic cell comprising a recombinant protein are also well known in the art and further detailed in the Examples.

(ii) A First Protein Linked to a First Reporter and a Second Protein Linked to a Second Reporter In another aspect of the invention, a method of the invention encompasses a first protein linked to a first reporter and a second protein linked to a second reporter, wherein the first protein and the second protein aggregate producing a detectable signal. Said another way, the first and second protein, each a recombinant protein linked to a unique reporter, act together as an intracellular "biosensor" that produces a detectable signal when the first and second protein aggregate.

In some embodiments, a first protein linked to a first reporter and a second protein linked to a second reporter each comprise a similar aggregation-prone domain. Hence, the interaction between the aggregation-prone domains causes the first protein and the second protein to aggregate. Suitable aggregation-prone domains are described above in Section A. As used herein, "similar" refers to the degree of sequence identity between the two aggregation-prone domains. One skilled in the art will appreciate that the interactions mediating aggregation do not require absolute sequence identity (for example, hydrophobic interactions mediate aggregation and may occur between any two polar amino acids). Sequence similarity may be determined using known methods in the art, including, but not limited to, BLASTP programs. In certain embodiments, a first protein linked to a first reporter and a second protein linked to a second reporter each comprise an aggregation-prone domain from the same protein.

In other embodiments, a first protein linked to a first reporter and a second protein linked to a second reporter each comprise an aggregation-prone domain from a different protein. For example, synuclein and tau have been described to "co-aggregate" in vitro, and appear to co-occur in aggregated form in various neurodegenerative diseases.

According to the invention, a detectable signal is used to report the occurrence of protein aggregation. Use of fluorescence resonance energy transfer (FRET) and protein fragment complementation as a reporter strategy can accurately and rapidly dissect protein interactions (including protein aggregation) with a variety of readouts, including absorbance, fluorescence, and bioluminescence. However, one skilled in the art will appreciate that any suitable method to detect and quantify protein-protein interactions in vivo may be alternatively used.

In some embodiments, a detectable signal may be a FRET signal. When the detectable signal is a FRET signal, the FRET energy donor may be the first reporter and the FRET energy acceptor may be the second reporter. Alternatively, the FRET energy donor may be the second reporter and the FRET energy acceptor may be the first reporter. Any number of FRET donor/acceptor pairs are known to one of skill in the art and can be used. In a preferred embodiment, the detectable signal is a FRET signal and the first and second reporter are selected from the group consisting of CFP and YFP.

In other embodiments, a detectable signal may be a bioluminescent signal. When the detectable signal is a bioluminescent signal, a split-luciferase is used to produce the bioluminescence from a substrate, and the first and second reporters are the amino- (NLuc) and carboxy- (CLuc) terminal fragments of the luciferase. Non-limiting examples of a luciferase that may be used include *Renilla*, firefly (including, but not limited to, *Phontinus pyralis*), click beetle, and *Metridia* luciferase. In a preferred embodiment, a detectable signal is a bioluminescent signal and the first and second reporter are selected from the group consisting of NLuc and CLuc fragments of click beetle luciferase.

In preferred embodiments, a first protein linked to a first reporter and a second protein linked to a second reporter each comprise a similar aggregation-prone domain, wherein the aggregation-prone domain is an aggregation-prone domain of a pathological protein, and the pathological protein is selected from the group consisting of tau, synuclein, htt, AR, superoxide dismutase, prion protein, amyloid beta, TDP-43, serpin, transthyretin, PABPN1 and ataxin.

Methods of making a recombinant protein are well known in the art, and may include introducing a deletion, substitution, addition or insertion into the nucleic acid sequence encoding the protein in order to make a recombinant protein of the invention. Such alterations may be generated using recombinant techniques well-known in the art. Additional information may be found in Sambrook et al., Molecular Cloning: A Laboratory Manual (New York: Cold Spring Harbor Laboratory Press, 1989). The first protein linked to a first reporter and a second protein linked to a second reporter can be transiently expressed in a eukaryotic cell or can be stably expressed in a eukaryotic cell, as detailed in the Example. Stable cell lines with high signal to noise ratio may be identified by screening sub-populations of cells for expression level.

C. Biological Sample

In another aspect, a method of the invention encompasses contacting the at least one eukaryotic cell with a biological sample comprising a protein aggregate, such that the protein aggregate is taken up by the cell. The biosensor system will not respond to any aggregate in a biological sample, but only to aggregates derived from the same type of protein or aggregates with similar aggregation-prone domains. The aggregation-prone domains must be similar in order for the intracellular biosensor to be able to sense and respond to the protein aggregate in the biological sample. Suitable protein aggregates and aggregation-prone domains are described above in Section A.

Generally, a biological sample needs to be in contact with at least one eukaryotic cell of the invention for a sufficient amount of time to allow a protein aggregate in the biological sample to be taken up by the cell. In some embodiments, the biological sample is in contact with the at least one mammalian cell for about 30 minutes to about 24 hours. For example, the biological sample may in contact with the at least one mammalian cell for about 30 minutes, about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours. In exemplary embodiments, the biological sample is in contact with the at least one mammalian cell for about 30 minutes to about 1 hour. In other exemplary embodiments, the biological sample is in contact with the at least one mammalian cell for at least 1 hour. In other exemplary embodiments, the biological sample is in contact with the at least one mammalian cell at least 6 hours. In other exemplary embodiments, the biological sample is in contact with the at least one mammalian cell for at least 12 hours. In a preferred embodiment, the biological sample is in contact with the mammalian cell for at least 4 hours.

As used herein, "biological sample" refers to a sample derived from a subject. Suitable subjects may include a human, a livestock animal, a companion animal, a lab animal, or a zoological animal. In one embodiment, a subject may be a rodent, e.g. a mouse, a rat, a guinea pig, etc. In another embodiment, a subject may be a livestock animal. Non-limiting examples of suitable livestock animals may include pigs, cows, horses, goats, sheep, llamas and alpacas. In yet another embodiment, a subject may be a companion animal. Non-limiting examples of companion animals may include pets such as dogs, cats, rabbits, and birds. In yet another embodiment, a subject may be a zoological animal. As used herein, a "zoological animal" refers to an animal that may be found in a zoo. Such animals may include non-human primates, large cats, wolves, and bears. In a preferred embodiment, a subject is human.

A method of the invention may be used with any of the numerous types of biological samples known in the art. Non-limiting examples may include tissue samples or bodily fluids. In some embodiments, a biological sample is a tissue sample such as a tissue biopsy. The tissue biopsy may be a brain biopsy, a spinal cord biopsy or a CNS microvascular biopsy. The biopsied tissue may be fixed, embedded in paraffin or plastic, and sectioned, or the biopsied tissue may be frozen and cryosectioned. Alternatively, a biopsied tissue may be processed into individual cells or an explant, or processed into a homogenate, a cell extract, or a membranous fraction. A sample may also be primary and/or transformed cell cultures derived from tissue from a subject. In other embodiments, a sample may be a bodily fluid. Non-limiting examples of bodily fluids include cerebrospinal fluid, interstitial fluid, blood, serum, plasma, saliva, sputum, semen, tears, and urine. The fluid may be used "as is", the cellular components may be isolated from the fluid, or a protein faction may be isolated from the fluid using standard techniques. For example, a sample of cerebrospinal fluid may be fractionated into individual cellular components using techniques that are well known to those with skill in the art. In preferred embodiments, a sample may be cerebrospinal fluid, blood, plasma or serum.

As will be appreciated by a skilled artisan, the method of collecting a biological sample can and will vary depending upon the nature of the biological sample. Any of a variety of methods generally known in the art may be utilized to collect a biological sample. Generally speaking, the method preferably maintains the integrity of the protein aggregate such that it can be accurately measured according to the method of the invention. Further processing of a biological sample may be necessary after collection of the biological sample but before contacting the biological sample with a mammalian cell-based assay.

In some embodiments, a method of the invention further comprises adjusting the concentration of a protein aggregate in a biological sample prior to contacting the biological sample with a mammalian cell-based assay. For example, a biological sample may need to be diluted if the amount of a protein aggregate is above the limit of detection of the assay. Biological samples may be diluted in any appropriate buffer or medium. In exemplary embodiments, a biological samples may be diluted about 1:5 to about 1:100. For example, a biological sample may be diluted about 1:5, about 1:10, about 1:15, about 1:20, about 1:25, about 1:30, about 1:35, about 1:40, about 1:45, about 1:50, about 1:55, about 1:60, about 1:65, about 1:70, about 1:75, about 1:80, about 1:85, about 1:90, about 1:95, about 1:100. Alternatively, a biological sample may first be concentrated if the amount of the protein aggregate is below the limit of detection of the assay. Methods of concentrating proteins in a biological sample are well known in the art. In some exemplary embodiments, biological samples are concentrated about 1:5 to about 1:2000. For example, a biological sample may be concentrated about 1:5, about 1:10, about 1:15, about 1:20, about 1:25, about 1:30, about 1:35, about 1:40, about 1:45, about 1:50, about 1:55, about 1:60, about 1:65, about 1:70, about 1:75, about 1:80, about 1:85, about 1:90, about 1:95, or about 1:100. Alternatively, a biological sample may be concentrated about 1:150, about 1:200, about 1:250, about 1:300, about 1:350, about 1:400, about 1:450, about 1:500, about 1:550, about 1:600, about 1:650, about 1:700, about 1:750, about 1:800, about 1:850, about 1:900, about 1:950, about 1:1000, about 1:1050, about 1:1100, about 1:1150, about 1:1200, about 1:1250, about 1:1300, about 1:1350, about 1:1400, about 1:1450, about 1:1500, about 1:1550, about 1:1600, about 1:1650, about 1:1700, about 1:1750, about 1:1800, about 1:1850, about 1:1900, about 1:1950, or about 1:2000. In other exemplary embodiments, biological samples are concentrated at least 1:2000. For examples, a biological sample may be concentrated at least 1:3000, at least 1:4000, at least 1:5000, at least 1:6000, at least 1:7000, at least 1:8000, at least 1:9000, at least 1:10,000, at least 1:11,000, at least 1:12,000, at least 1:13,000, at least 1:14,000, at least 1:15,000, at least 1:16,000, at least 1:17,000, at least 1:18,000, at least 1:19,000, or at least 1:20,000.

In other embodiments, a method fo the invention further comprises separating a protein aggregate from other components of a biological sample prior to contacting the biological sample with a mammalian cell-based assay (e.g. other proteins, lipids, carbohydrates, etc). For example, the seeding activity of a sample may be enriched by applying a purified protein aggregate to a mammalian cell-based assay, thereby increasing the sensitivity and specificity of the assay. A protein aggregate may be partially or completely purified. For example, a protein aggregate may be at least 1%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100% purified from other components in a biological sample, as determined by standard methodology known in the art. Suitable methods to separate a protein aggregate from other components of a biological sample include, but are not limited to, chromatography, immunoprecipitation, affinity purification, and adsorption.

In other embodiments, a method of the invention further comprises breaking apart the protein aggregates prior to contacting the biological sample with the mammalian cell-based assay. For example, protein aggregates in the biological sample may be too large to be taken up by the cell, requiring the protein aggregates to be broken apart into smaller protein aggregates. Alternatively, protein aggregates may be deposited in inclusion bodies or otherwise encapsulated in some other vesicle, requiring these vesicles to be broken apart in order to properly expose the protein aggregates to the biosensor. Suitable methods to break apart protein aggregates or disrupt vesicles may include, but is not limited to, sonication. In certain other embodiments, lipid-based transfection reagent may be used to transduce seeds directly into the cytosol of a biosensor cell line. Lipid-based transfection reagents are well-known in the art and may include, but are not limited to, Lipofectamine 2000. In exemplary embodiments, biological samples are sonicated for about 30 to about 60 seconds prior to contacting the biological sample with the mammalian cell-based assay. In other exemplary embodiments, a lipid-based transfection reagent is added to a biological sample prior to contacting the biological sample with the mammalian cell-based assay.

D. Measuring a Detectable Signal

In another aspect, the invention encompasses measuring a detectable signal. In some embodiments, a measurement is qualitative. In other embodiments, a measurement is semi-quantitative. In still other embodiments, a measurement is a quantitative. Detection systems to detect and optionally quantify a detectable signal (e.g. fluorescence or bioluminescence) are well known in the art. Non-limiting examples of suitable fluorescence detection systems include spectrofluoremeters and microplate readers, fluorescence microscopes, fluorescence scanners, and flow cytometers. Suitable bioluminescent detection systems are also well known in the art. For instance, CCD cameras are typically used to detect and quantify the conversion of the bioluminescent substrate into light and can be equipped to devices including, but not limited to, microscopes, scanners, and microplate readers. One skilled in the art will appreciate that the choice of the detection system may depend in part on the type and number of samples.

Measurements may be made in the presence or absence of a biological sample. In some embodiments, a measurement occurs in the presence of a biological sample. In other embodiments, a measurement occurs in the absence of a biological sample. When a measurement is made in the absence of a biological sample, typically the cell culture medium is replaced with fresh medium, thereby removing the biological sample.

The dynamic range of a detectable signal that can be measured by a method of the invention provides an improvement over previous methods known in the art. Advantageously, a method of the invention has the sensitivity to detect the presence of protein aggregates in biological samples that previous methods were not able to measure. Typically, a method of the invention measures a detectable signal that corresponds to a concentration of monomer-equivalents of about 1 pM to about 100 nM. In some embodiments, a method of the invention measures a detectable signal that corresponds to a concentration of monomer-equivalents of about 1 pM to about 0.100 nM. For example, the concentration of monomer-equivalents may be about 0.001, 0.005, 0.010, 0.015, 0.020, 0.025, 0.030, 0.035, 0.040, 0.045, 0.050, 0.050, 0.060, 0.065, 0.070, 0.075, 0.080, 0.085, 0.090, 0.095, 0.100, 0.150, 0.200, 0.250, 0.300, 0.350, 0.400, 0.450, 0.500, 0.550, 0.600, 0.650, 0.700, 0.750, 0.800, 0.850, 0.900, 0.950, 1.000, 1.050, 1.100, 1.150, 1.200, 1.250, 1.300, 1.350, 1.400, 1.450, 1.500, 1.550, 1.600, 1.650, 1.700, 1.750, 1.800, 1.850, 1.900, 1.950, 2.000, 2.050, 2.100, 2.150, 2.200, 2.250, 2.300, 2.350, 2.400, 2.450, 2.500, 2.550, 2.600, 2.650, 2.700, 2.750, 2.800, 2.850, 2.900, 2.950, 3.000, 3.050, 3.100, 3.150, 3.200, 3.250, 3.300, 3.350, 3.400, 3.450, 3.500, 3.550, 3.600, 3.650, 3.700, 3.750, 3.800, 3.850, 3.900, 3.950, 4.000, 4.050, 4.100, 4.150, 4.200, 4.250, 4.300, 4.350, 4.400, 4.450, 4.500, 4.550, 4.600, 4.650, 4.700, 4.750, 4.800, 4.850, 4.900, 4.950, 5.000, 5.050, 5.100, 5.150, 5.200, 5.250, 5.300, 5.350, 5.400, 5.450, 5.500, 5.550, 5.600, 5.650, 5.700, 5.750, 5.800, 5.850, 5.900, 5.950, 6.000, 6.050, 6.100, 6.150, 6.200, 6.250, 6.300, 6.350, 6.400, 6.450, 6.500, 6.550, 6.600, 6.650, 6.700, 6.750, 6.800, 6.850, 6.900, 6.950, 7.000, 7.050, 7.100, 7.150, 7.200, 7.250, 7.300, 7.350, 7.400, 7.450, 7.500, 7.550, 7.600, 7.650, 7.700, 7.750, 7.800, 7.850, 7.900, 7.950, 8.000, 8.050, 8.100, 8.150, 8.200, 8.250, 8.300, 8.350, 8.400, 8.450, 8.500, 8.550, 8.600, 8.650, 8.700, 8.750, 8.800, 8.850, 8.900, 8.950, 9.000, 9.050, 9.100, 9.150, 9.175, 9.200, 9.250, 9.300, 9.350, 9.400, 9.450, 9.500, 9.550, 9.600, 9.650, 9.700, 9.800, 9.850, 9.900, 9.950, 10.000, 10.010, 10.015, 10.020, 10.025, 10.030, 10.035, 10.040, 10.045, 10.050, 10.050, 10.060, 10.065, 10.070, 10.075, 10.080, 10.085, 10.090, 10.095, 10.100, 10.150, 10.200, 10.250, 10.300, 10.350, 10.400, 10.450, 10.500, 10.550, 10.600, 10.650, 10.700, 10.750, 10.800, 10.850, 10.900, 10.950, 11.000, 11.050, 11.100, 11.150, 11.200, 11.250, 11.300, 11.350, 11.400, 11.450, 11.500, 11.550, 11.600, 11.650, 11.700, 11.750, 11.800, 11.850, 11.900, 11.950, 12.000, 12.050, 12.100, 12.150, 12.200, 12.250, 12.300, 12.350, 12.400, 12.450, 12.500, 12.550, 12.600, 12.650, 12.700, 12.750, 12.800, 12.850, 12.900, 12.950, 13.000, 13.050, 13.100, 13.150, 13.200, 13.250, 13.300, 13.350, 13.400, 13.450, 13.500, 13.550, 13.600, 13.650, 13.700, 13.750, 13.800, 13.850, 13.900, 13.950, 14.000, 14.050, 14.100, 14.150, 14.200, 14.250, 14.300, 14.350, 14.400, 14.450, 14.500, 14.550, 14.600, 14.650, 14.700, 14.750, 14.800, 14.850, 14.900, 14.950, 15.000, 15.050, 15.100, 15.150, 15.200, 15.250, 15.300, 15.350, 15.400, 15.450, 15.500, 15.550, 15.600, 15.650, 15.700, 15.750, 15.800, 15.850, 15.900, 15.950, 16.000, 16.050, 16.100, 16.150, 16.200, 16.250, 16.300, 16.350, 16.400, 16.450, 16.500, 16.550, 16.600, 16.650, 16.700, 16.750, 16.800, 16.850, 16.900, 16.950, 17.000, 17.050, 17.100, 17.150, 17.200, 17.250, 17.300, 17.350, 17.400, 17.450, 17.500, 17.550, 17.600, 17.650, 17.700, 17.750, 17.800, 17.850, 17.900, 17.950, 18.000, 18.050, 18.100, 18.150, 18.200, 18.250, 18.300, 18.350, 18.400, 18.450, 18.500, 18.550, 18.600, 18.650, 18.700, 18.750, 18.800, 18.850, 18.900, 18.950, 19.000, 19.050, 19.100, 19.150, 19.175, 19.200, 19.250, 19.300, 19.350, 19.400, 19.450, 19.500, 19.550, 19.600, 19.650, 19.700, 19.800, 19.850, 19.900, 19.950, 20.000 20.010, 20.015, 20.020, 20.025, 20.030, 20.035, 20.040, 20.045, 20.050, 20.050, 20.060, 20.065, 20.070, 20.075, 20.080, 20.085, 20.090, 20.095, 20.100, 20.150, 20.200, 20.250, 20.300, 20.350, 20.400, 20.450, 20.500, 20.550, 20.600, 20.650, 20.700, 20.750, 20.800, 20.850, 20.900, 20.950, 21.000, 21.050, 21.100, 21.150, 21.200, 21.250, 21.300, 21.350, 21.400, 21.450, 21.500, 21.550, 21.600, 21.650, 21.700, 21.750, 21.800, 21.850, 21.900, 21.950, 22.000, 22.050, 22.100, 22.150, 22.200, 22.250, 22.300, 22.350, 22.400, 22.450, 22.500, 22.550, 22.600, 22.650, 22.700, 22.750, 22.800, 22.850, 22.900, 22.950, 23.000, 23.050, 23.100, 23.150, 23.200, 23.250, 23.300, 23.350, 23.400, 23.450, 23.500, 23.550, 23.600, 23.650, 23.700, 23.750, 23.800, 23.850, 23.900, 23.950, 24.000, 24.050, 24.100, 24.150, 24.200, 24.250, 24.300, 24.350, 24.400, 24.450, 24.500, 24.550, 24.600, 24.650, 24.700, 24.750, 24.800, 24.850, 24.900, 24.950, 25.000, 25.050, 25.100, 25.150, 25.200, 25.250, 25.300, 25.350, 25.400, 25.450, 25.500, 25.550, 25.600, 25.650, 25.700, 25.750, 25.800, 25.850, 25.900, 25.950, 26.000, 26.050, 26.100, 26.150, 26.200, 26.250, 26.300, 26.350, 26.400, 26.450, 26.500, 26.550, 26.600, 26.650, 26.700, 26.750, 26.800, 26.850, 26.900, 26.950, 27.000, 27.050, 27.100, 27.150, 27.200, 27.250, 27.300, 27.350, 27.400, 27.450, 27.500, 27.550, 27.600, 27.650, 27.700, 27.750, 27.800, 27.850, 27.900, 27.950, 28.000, 28.050, 28.100, 28.150, 28.200, 28.250, 28.300, 28.350, 28.400, 28.450, 28.500, 28.550, 28.600, 28.650, 28.700, 28.750, 28.800, 28.850, 28.900, 28.950, 29.000, 29.050, 29.100, 29.150, 29.175, 29.200, 29.250, 29.300, 29.350, 29.400, 29.450, 29.500, 29.550, 29.600, 29.650, 29.700, 29.800, 29.850, 29.900, 29.950, 30.000, 30.010, 30.015, 30.020, 30.025, 30.030, 30.035, 30.040, 30.045, 30.050, 30.050, 30.060, 30.065, 30.070, 30.075, 30.080, 30.085, 30.090, 30.095, 30.100, 30.150, 30.200, 30.250, 30.300, 30.350, 30.400, 30.450, 30.500, 30.550, 30.600, 30.650, 30.700, 30.750, 30.800, 30.850, 30.900, 30.950, 31.000, 31.050, 31.100, 31.150, 31.200, 31.250, 31.300, 31.350, 31.400, 31.450, 31.500, 31.550, 31.600, 31.650, 31.700, 31.750, 31.800, 31.850, 31.900, 31.950, 32.000, 32.050, 32.100, 32.150, 32.200, 32.250, 32.300, 32.350, 32.400, 32.450, 32.500, 32.550, 32.600, 32.650, 32.700, 32.750, 32.800, 32.850, 32.900, 32.950, 33.000, 33.050, 33.100, 33.150, 33.200, 33.250, 33.300, 33.350, 33.400, 33.450, 33.500, 33.550, 33.600, 33.650, 33.700, 33.750, 33.800, 33.850, 33.900, 33.950, 34.000, 34.050, 34.100, 34.150, 34.200, 34.250, 34.300, 34.350, 34.400, 34.450, 34.500, 34.550, 34.600, 34.650, 34.700, 34.750, 34.800, 34.850, 34.900, 34.950, 35.000, 35.050, 35.100, 35.150, 35.200, 35.250, 35.300, 35.350, 35.400, 35.450, 35.500, 35.550, 35.600, 35.650, 35.700, 35.750, 35.800, 35.850, 35.900, 35.950, 36.000, 36.050, 36.100, 36.150, 36.200, 36.250, 36.300, 36.350, 36.400, 36.450, 36.500, 36.550, 36.600, 36.650, 36.700, 36.750, 36.800, 36.850, 36.900, 36.950, 37.000, 37.050, 37.100, 37.150, 37.200, 37.250, 37.300, 37.350, 37.400, 37.450, 37.500, 37.550, 37.600, 37.650, 37.700, 37.750, 37.800, 37.850, 37.900, 37.950, 38.000, 38.050, 38.100, 38.150, 38.200, 38.250, 38.300, 38.350, 38.400, 38.450, 38.500, 38.550, 38.600, 38.650, 38.700, 38.750, 38.800, 38.850, 38.900, 38.950, 39.000, 39.050, 39.100, 39.150, 39.175, 39.200, 39.250, 39.300, 39.350, 39.400, 39.450, 39.500, 39.550, 39.600, 39.650, 39.700, 39.800, 39.850, 39.900, 39.950, 40.000, 40.010, 40.015, 40.020, 40.025, 40.030, 40.035, 40.040, 40.045, 40.050, 40.050, 40.060, 40.065, 40.070, 40.075, 40.080, 40.085, 40.090, 40.095, 40.100, 40.150, 40.200, 40.250, 40.300, 40.350, 40.400, 40.450, 40.500, 40.550, 40.600, 40.650, 40.700, 40.750, 40.800, 40.850, 40.900, 40.950, 41.000, 41.050, 41.100, 41.150, 41.200, 41.250, 41.300, 41.350, 41.400, 41.450, 41.500, 41.550, 41.600, 41.650, 41.700, 41.750, 41.800, 41.850, 41.900, 41.950, 42.000, 42.050, 42.100, 42.150, 42.200, 42.250, 42.300, 42.350, 42.400, 42.450, 42.500, 42.550, 42.600, 42.650, 42.700, 42.750, 42.800, 42.850, 42.900, 42.950, 43.000, 43.050, 43.100, 43.150, 43.200, 43.250, 43.300, 43.350, 43.400, 43.450, 43.500, 43.550, 43.600, 43.650, 43.700, 43.750, 43.800, 43.850, 43.900, 43.950, 44.000, 44.050, 44.100, 44.150, 44.200, 44.250, 44.300, 44.350, 44.400, 44.450, 44.500, 44.550, 44.600, 44.650, 44.700, 44.750, 44.800, 44.850, 44.900, 44.950, 45.000, 45.050, 45.100, 45.150, 45.200, 45.250, 45.300, 45.350, 45.400, 45.450, 45.500, 45.550, 45.600, 45.650, 45.700, 45.750, 45.800, 45.850, 45.900, 45.950, 46.000, 46.050, 46.100, 46.150, 46.200, 46.250, 46.300, 46.350, 46.400, 46.450, 46.500, 46.550, 46.600, 46.650, 46.700, 46.750, 46.800, 46.850, 46.900, 46.950, 47.000, 47.050, 47.100, 47.150, 47.200, 47.250, 47.300, 47.350, 47.400, 47.450, 47.500, 47.550, 47.600, 47.650, 47.700, 47.750, 47.800, 47.850, 47.900, 47.950, 48.000, 48.050, 48.100, 48.150, 48.200, 48.250, 48.300, 48.350, 48.400, 48.450, 48.500, 48.550, 48.600, 48.650, 48.700, 48.750, 48.800, 48.850, 48.900, 48.950, 49.000, 49.050, 49.100, 49.150, 49.175, 49.200, 49.250, 49.300, 49.350, 49.400, 49.450, 49.500, 49.550, 49.600, 49.650, 49.700, 49.800, 49.850, 49.900, 49.950, 50.000, 50.010, 50.015, 50.020, 50.025, 50.030, 50.035, 50.040, 50.045, 50.050, 50.050, 50.060, 50.065, 50.070, 50.075, 50.080, 50.085, 50.090, 50.095, 50.100, 50.150, 50.200, 50.250, 50.300, 50.350, 50.400, 50.450, 50.500, 50.550, 50.600, 50.650, 50.700, 50.750, 50.800, 50.850, 50.900, 50.950, 51.000, 51.050, 51.100, 51.150, 51.200, 51.250, 51.300, 51.350, 51.400, 51.450, 51.500, 51.550, 51.600, 51.650, 51.700, 51.750, 51.800, 51.850, 51.900, 51.950, 52.000, 52.050, 52.100, 52.150, 52.200, 52.250, 52.300, 52.350, 52.400, 52.450, 52.500, 52.550, 52.600, 52.650, 52.700, 52.750, 52.800, 52.850, 52.900, 52.950, 53.000, 53.050, 53.100, 53.150, 53.200, 53.250, 53.300, 53.350, 53.400, 53.450, 53.500, 53.550, 53.600, 53.650, 53.700, 53.750, 53.800, 53.850, 53.900, 53.950, 54.000, 54.050, 54.100, 54.150, 54.200, 54.250, 54.300, 54.350, 54.400, 54.450, 54.500, 54.550, 54.600, 54.650, 54.700, 54.750, 54.800, 54.850, 54.900, 54.950, 55.000, 55.050, 55.100, 55.150, 55.200, 55.250, 55.300, 55.350, 55.400, 55.450, 55.500, 55.550, 55.600, 55.650, 55.700, 55.750, 55.800, 55.850, 55.900, 55.950, 56.000, 56.050, 56.100, 56.150, 56.200, 56.250, 56.300, 56.350, 56.400, 56.450, 56.500, 56.550, 56.600, 56.650, 56.700, 56.750, 56.800, 56.850, 56.900, 56.950, 57.000, 57.050, 57.100, 57.150, 57.200, 57.250, 57.300, 57.350, 57.400, 57.450, 57.500, 57.550, 57.600, 57.650, 57.700, 57.750, 57.800, 57.850, 57.900, 57.950, 58.000, 58.050, 58.100, 58.150, 58.200, 58.250, 58.300, 58.350, 58.400, 58.450, 58.500, 58.550, 58.600, 58.650, 58.700, 58.750, 58.800, 58.850, 58.900, 58.950, 59.000, 59.050, 59.100, 59.150, 59.175, 59.200, 59.250, 59.300, 59.350, 59.400, 59.450, 59.500, 59.550, 59.600, 59.650, 59.700, 59.800, 59.850, 59.900, 59.950, 60.000, 60.010, 60.015, 60.020, 60.025, 60.030, 60.035, 60.040, 60.045, 60.050, 60.050, 60.060, 60.065, 60.070, 60.075, 60.080, 60.085, 60.090, 60.095, 60.100, 60.150, 60.200, 60.250, 60.300, 60.350, 60.400, 60.450, 60.500, 60.550, 60.600, 60.650, 60.700, 60.750, 60.800, 60.850, 60.900, 60.950, 61.000, 61.050, 61.100, 61.150, 61.200, 61.250, 61.300, 61.350, 61.400, 61.450, 61.500, 61.550, 61.600, 61.650, 61.700, 61.750, 61.800, 61.850, 61.900, 61.950, 62.000, 62.050, 62.100, 62.150, 62.200, 62.250, 62.300, 62.350, 62.400, 62.450, 62.500, 62.550, 62.600, 62.650, 62.700, 62.750, 62.800, 62.850, 62.900, 62.950, 63.000, 63.050, 63.100, 63.150, 63.200, 63.250, 63.300, 63.350, 63.400, 63.450, 63.500, 63.550, 63.600, 63.650, 63.700, 63.750, 63.800, 63.850, 63.900, 63.950, 64.000, 64.050, 64.100, 64.150, 64.200, 64.250, 64.300, 64.350, 64.400, 64.450, 64.500, 64.550, 64.600, 64.650, 64.700, 64.750, 64.800, 64.850, 64.900, 64.950, 65.000, 65.050, 65.100, 65.150, 65.200, 65.250, 65.300, 65.350, 65.400, 65.450, 65.500, 65.550, 65.600, 65.650, 65.700, 65.750, 65.800, 65.850, 65.900, 65.950, 66.000, 66.050, 66.100, 66.150, 66.200, 66.250, 66.300, 66.350, 66.400, 66.450, 66.500, 66.550, 66.600, 66.650, 66.700, 66.750, 66.800, 66.850, 66.900, 66.950, 67.000, 67.050, 67.100, 67.150, 67.200, 67.250, 67.300, 67.350, 67.400, 67.450, 67.500, 67.550, 67.600, 67.650, 67.700, 67.750, 67.800, 67.850, 67.900, 67.950, 68.000, 68.050, 68.100, 68.150, 68.200, 68.250, 68.300, 68.350, 68.400, 68.450, 68.500, 68.550, 68.600, 68.650, 68.700, 68.750, 68.800, 68.850, 68.900, 68.950, 69.000, 69.050, 69.100, 69.150, 69.175, 69.200, 69.250, 69.300, 69.350, 69.400, 69.450, 69.500, 69.550, 69.600, 69.650, 69.700, 69.800, 69.850, 69.900, 69.950, 70.000, 70.010, 70.015, 70.020, 70.025, 70.030, 70.035, 70.040, 70.045, 70.050, 70.050, 70.060, 70.065, 70.070, 70.075, 70.080, 70.085, 70.090, 70.095, 70.100, 70.150, 70.200, 70.250, 70.300, 70.350, 70.400, 70.450, 70.500, 70.550, 70.600, 70.650, 70.700, 70.750, 70.800, 70.850, 70.900, 70.950, 71.000, 71.050, 71.100, 71.150, 71.200, 71.250, 71.300, 71.350, 71.400, 71.450, 71.500, 71.550, 71.600, 71.650, 71.700, 71.750, 71.800, 71.850, 71.900, 71.950, 72.000, 72.050, 72.100, 72.150, 72.200, 72.250, 72.300, 72.350, 72.400, 72.450, 72.500, 72.550, 72.600, 72.650, 72.700, 72.750, 72.800, 72.850, 72.900, 72.950, 73.000, 73.050, 73.100, 73.150, 73.200, 73.250, 73.300, 73.350, 73.400, 73.450, 73.500, 73.550, 73.600, 73.650, 73.700, 73.750, 73.800, 73.850, 73.900, 73.950, 74.000, 74.050, 74.100, 74.150, 74.200, 74.250, 74.300, 74.350, 74.400, 74.450, 74.500, 74.550, 74.600, 74.650, 74.700, 74.750, 74.800, 74.850, 74.900, 74.950, 75.000, 75.050, 75.100, 75.150, 75.200, 75.250, 75.300, 75.350, 75.400, 75.450, 75.500, 75.550, 75.600, 75.650, 75.700, 75.750, 75.800, 75.850, 75.900, 75.950, 76.000, 76.050, 76.100, 76.150, 76.200, 76.250, 76.300, 76.350, 76.400, 76.450, 76.500, 76.550, 76.600, 76.650, 76.700, 76.750, 76.800, 76.850, 76.900, 76.950, 77.000, 77.050, 77.100, 77.150, 77.200, 77.250, 77.300, 77.350, 77.400, 77.450, 77.500, 77.550, 77.600, 77.650, 77.700, 77.750, 77.800, 77.850, 77.900, 77.950, 78.000, 78.050, 78.100, 78.150, 78.200, 78.250, 78.300, 78.350, 78.400, 78.450, 78.500, 78.550, 78.600, 78.650, 78.700, 78.750, 78.800, 78.850, 78.900, 78.950, 79.000, 79.050, 79.100, 79.150, 79.175, 79.200, 79.250, 79.300, 79.350, 79.400, 79.450, 79.500, 79.550, 79.600, 79.650, 79.700, 79.800, 79.850, 79.900, 79.950, 80.000, 80.010, 80.015, 80.020, 80.025, 80.030, 80.035, 80.040, 80.045, 80.050, 80.050, 80.060, 80.065, 80.070, 80.075, 80.080, 80.085, 80.090, 80.095, 80.100, 80.150, 80.200, 80.250, 80.300, 80.350, 80.400, 80.450, 80.500, 80.550, 80.600, 80.650, 80.700, 80.750, 80.800, 80.850, 80.900, 80.950, 81.000, 81.050, 81.100, 81.150, 81.200, 81.250, 81.300, 81.350, 81.400, 81.450, 81.500, 81.550, 81.600, 81.650, 81.700, 81.750, 81.800, 81.850, 81.900, 81.950, 82.000, 82.050, 82.100, 82.150, 82.200, 82.250, 82.300, 82.350, 82.400, 82.450, 82.500, 82.550, 82.600, 82.650, 82.700, 82.750, 82.800, 82.850, 82.900, 82.950, 83.000, 83.050, 83.100, 83.150, 83.200, 83.250, 83.300, 83.350, 83.400, 83.450, 83.500, 83.550, 83.600, 83.650, 83.700, 83.750, 83.800, 83.850, 83.900, 83.950, 84.000, 84.050, 84.100, 84.150, 84.200, 84.250, 84.300, 84.350, 84.400, 84.450, 84.500, 84.550, 84.600, 84.650, 84.700, 84.750, 84.800, 84.850, 84.900, 84.950, 85.000, 85.050, 85.100, 85.150, 85.200, 85.250, 85.300, 85.350, 85.400, 85.450, 85.500, 85.550, 85.600, 85.650, 85.700, 85.750, 85.800, 85.850, 85.900, 85.950, 86.000, 86.050, 86.100, 86.150, 86.200, 86.250, 86.300, 86.350, 86.400, 86.450, 86.500, 86.550, 86.600, 86.650, 86.700, 86.750, 86.800, 86.850, 86.900, 86.950, 87.000, 87.050, 87.100, 87.150, 87.200, 87.250, 87.300, 87.350, 87.400, 87.450, 87.500, 87.550, 87.600, 87.650, 87.700, 87.750, 87.800, 87.850, 87.900, 87.950, 88.000, 88.050, 88.100, 88.150, 88.200, 88.250, 88.300, 88.350, 88.400, 88.450, 88.500, 88.550, 88.600, 88.650, 88.700, 88.750, 88.800, 88.850, 88.900, 88.950, 89.000, 89.050, 89.100, 89.150, 89.175, 89.200, 89.250, 89.300, 89.350, 89.400, 89.450, 89.500, 89.550, 89.600, 89.650, 89.700, 89.800, 89.850, 89.900, 89.950, 90.000, 90.010, 90.015, 90.020, 90.025, 90.030, 90.035, 90.040, 90.045, 90.050, 90.050, 90.060, 90.065, 90.070, 90.075, 90.080, 90.085, 90.090, 90.095, 90.100, 90.150, 90.200, 90.250, 90.300, 90.350, 90.400, 90.450, 90.500, 90.550, 90.600, 90.650, 90.700, 90.750, 90.800, 90.850, 90.900, 90.950, 91.000, 91.050, 91.100, 91.150, 91.200, 91.250, 91.300, 91.350, 91.400, 91.450, 91.500, 91.550, 91.600, 91.650, 91.700, 91.750, 91.800, 91.850, 91.900, 91.950, 92.000, 92.050, 92.100, 92.150, 92.200, 92.250, 92.300, 92.350, 92.400, 92.450, 92.500, 92.550, 92.600, 92.650, 92.700, 92.750, 92.800, 92.850, 92.900, 92.950, 93.000, 93.050, 93.100, 93.150, 93.200, 93.250, 93.300, 93.350, 93.400, 93.450, 93.500, 93.550, 93.600, 93.650, 93.700, 93.750, 93.800, 93.850, 93.900, 93.950, 94.000, 94.050, 94.100, 94.150, 94.200, 94.250, 94.300, 94.350, 94.400, 94.450, 94.500, 94.550, 94.600, 94.650, 94.700, 94.750, 94.800, 94.850, 94.900, 94.950, 95.000, 95.050, 95.100, 95.150, 95.200, 95.250, 95.300, 95.350, 95.400, 95.450, 95.500, 95.550, 95.600, 95.650, 95.700, 95.750, 95.800, 95.850, 95.900, 95.950, 96.000, 96.050, 96.100, 96.150, 96.200, 96.250, 96.300, 96.350, 96.400, 96.450, 96.500, 96.550, 96.600, 96.650, 96.700, 96.750, 96.800, 96.850, 96.900, 96.950, 97.000, 97.050, 97.100, 97.150, 97.200, 97.250, 97.300, 97.350, 97.400, 97.450, 97.500, 97.550, 97.600, 97.650, 97.700, 97.750, 97.800, 97.850, 97.900, 97.950, 98.000, 98.050, 98.100, 98.150, 98.200, 98.250, 98.300, 98.350, 98.400, 98.450, 98.500, 98.550, 98.600, 98.650, 98.700, 98.750, 98.800, 98.850, 98.900, 98.950, 99.000, 99.050, 99.100, 99.150, 99.175, 99.200, 99.250, 99.300, 99.350, 99.400, 99.450, 99.500, 99.550, 99.600, 99.650, 99.700, 99.800, 99.850, 99.900, 99.950, or 100.000 nM. In other embodiments, a method of the invention measures a detectable signal that corresponds to a concentration of monomer-equivalents of about 1 pM to about 1.000 nM. In still other embodiments, a method of the invention measures a detectable signal that corresponds to a concentration of monomer-equivalents of about 1.000 nM to about 10.000 nM. In yet other embodiments, a method of the invention measures a detectable signal that corresponds to a concentration of monomer-equivalents of about 10.000 nM to about 100.000 nM. In alternative embodiments, a method of the invention measures a detectable signal that corresponds to a concentration of monomer-equivalents of about 0.010 nM to about 100.000 nM. In other alternative embodiments, a method of the invention measures a detectable signal that corresponds to a concentration of monomer-equivalents of about 0.100 nM to about 50.000 nM. In still other alternative embodiments, a method of the invention measures a detectable signal that corresponds to a concentration of monomer-equivalents of about 0.100 nM to about 10.000 nM. In different embodiments, a method of the invention measures a detectable signal that corresponds to a concentration of monomer-equivalents of about 0.100 nM to about 100.000 nM. In still different embodiments, a method of the invention measures a detectable signal that corresponds to a concentration of monomer-equivalents of about 0.100 nM to about 50.000 nM.

E. Comparing to a Control

In another aspect, the invention encompasses comparing an amount of detectable signal produced by a biological sample to an amount of detectable signal produced by a control, wherein a change in the detectable signal indicates one or more protein aggregates are in the biological sample. A control may be an experimental control or a biological control. In general, the magnitude of the increase of the detectable signal in the biological sample compared to a control positively correlates with the amount of protein aggregate in the biological sample.

In some embodiments, a control is an experimental control. An experimental control, for example, may be a sample to which no biological sample was added. In exemplary embodiments, a control is a negative control. Non-limiting examples of a negative control include samples to which buffer or medium were added instead of a biological sample. As detailed in the Examples, the detectable signal from a negative control is used to establish the background signal. Hence, any increase in detectable signal in the biological sample relative to a negative control will indicate one or more aggregates in the biological sample. In other exemplary embodiments, a control is a positive control. Non-limiting examples of a positive control include samples to which a protein with an aggregate-prone domain or protein aggregate were added. Increasing amounts of a protein with an aggregate-prone domain or protein aggregate may be added in order to create a standard curve.

In some embodiments, a control is a biological control. A biological control may be a biological sample derived from a control subject. Within the context of this invention, a "control subject" is a subject or, more preferably, a population of subjects, that is/are known to not have abnormal protein aggregation. Suitable control subjects are well-known in the art, and are further detailed in the Examples.

In another iteration of the method, multiple biological samples may be collected from the same subject over time. Each biological sample may be compared to a negative control in order to determine the relative detectable signal at each timepoint the biological sample was collected. Then, the relative level of detectable signal may be compared between samples, wherein a change in the relative detectable signal indicates a change, either positive or negative, in the amount of protein aggregate in the biological sample over time.

In some embodiments, the fluorescence detection system is a plate reader and the detectable signal measured is an average change in fluorescence across a population of cells. In other embodiments, the fluorescence detection system is a flow cytometer and the detectable signal measured is an average change in fluorescence for an individual cell. Individual cells for analysis are gated for specific properties including living cells and single (i.e., not clumped) cells. "False FRET" arising from YFP emission into the FRET-channel is eliminated via an exclusion gate from control cells expressing YFP-tau RD only. FRET positive cells are identified by creating a bivariate plot for the FRET channel and the CFP channel. FRET positive cells are those that have increased FRET fluorescence and decreased CFP fluorescence. Suitable calculations and methods to report fluorescence are known in the art and may include Percent Positive Cells (the percentage of positive cells that reside within the FRET gate), Median Fluorescence Intensity (MFI; the median FRET intensity for the population that resides within the FRET gate); Integrated FRET Density (the product of Percent Cell Positive and MFI).

Pathology in most diseases with symptoms associated with pathological protein aggregation, such as those described in Section A, likely commences prior to diagnosis. Hence earlier awareness of pathological protein aggregation could lead to better outcomes if coupled with effective therapy to disrupt aggregation. Those of skill in the art will appreciate that the methods of the invention may be used to identify individuals with pathological protein aggregation prior to the onset of symptoms. Those of skill in the art will also appreciate that the method of the invention also may be used to monitor the progression of a disorder associated with pathological protein aggregation. Similarly, the method of the invention may also be used to monitor the effectiveness of therapy attempting to reduce protein aggregation. Typically, increasing levels of detectable signal (compared to a control subject or between biological samples collected over time) correlate with worsening of disease progression and/or lack of response to therapy, and decreasing levels of detectable signal (compared to a control subject or between biological samples collected over time) correlate with a reversal of disease progression and/or indicate response to therapy.

II. A METHOD FOR CLASSIFYING A SUBJECT BASED ON A THE SEEDING ACTIVITY OF THE SUBJECT'S BIOLOGICAL SAMPLE

As noted above, pathological protein aggregation likely commences prior to diagnosis or the onset of symptoms associated with pathological protein aggregation. Advantageously, the Applicants have discovered significant differences in the seeding activity of biological samples from subjects with symptoms of pathological protein aggregation and those without. As used herein, the "seeding activity" of a sample refers to the ability of a sample to nucleate (i.e. induce) aggregation of a protein with a similar aggregation domain as measured in vitro. It was also discovered that the seeding activity of biological samples from subjects without symptoms of pathological protein aggregation also varied significantly when subjects were followed over time for the development of these symptoms. Thus, the Applicant's have discovered that high seeding activity in a biological sample is a new biomarker for a subset of subjects that are more likely to develop symptoms of pathological protein aggregation.

In an aspect, the present invention provides a method for classifying a subject based on the seeding activity of the subject's biological sample. Typically the method comprises obtaining a biological sample from a subject, measuring the seeding activity of the sample, and classifying the subject as having high or low seeding activity.

In another aspect, the present invention provides a method for classifying a subject as being at risk for developing at least one symptom of pathological protein aggregation based on the seeding activity of a biological sample obtained from the subject. Typically the method comprises (i) obtaining a biological sample from a subject, (ii) measuring the seeding activity of the sample, wherein the seeding activity refers to the ability of a sample to nucleate aggregation of a pathological protein with a similar aggregation domain as measured in vitro, and (iii) classifying the subject as being at risk for developing at least one symptom of pathological protein aggregation if the seeding activity in the sample is high.

In another aspect, the present invention provides a method for classifying a subject as being at risk for developing a disease associated with pathological protein aggregation based on the seeding activity of a biological sample obtained from the subject. Typically the method comprises (i) obtaining a biological sample from a subject, (ii) measuring the seeding activity of the sample, wherein the seeding activity refers to the ability of a sample to nucleate aggregation of a pathological protein with a similar aggregation domain as measured in vitro, and (iii) classifying the subject as being at risk for developing a disease associated with pathological protein aggregation if the seeding activity in the sample is high.

Suitable samples are described above. In a preferred embodiment, a sample is brain lysate. In another preferred embodiment, a sample is CSF. In another preferred embodiment, a sample is plasma.

Suitable subjects are also described above. In some embodiments, a subject may have no symptoms of pathological protein aggregation. In other embodiments, a subject may have symptoms of pathological protein aggregation. In still other embodiments, a subject may be at risk for disease associated with pathological protein aggregation. In different embodiments, a subject may be diagnosed with disease associated with pathological protein aggregation.

As used herein, the phrase "at least one symptom associated with pathological protein aggregation" refers to any symptom caused by the formation of pathological protein aggregates. As used in the art, "a symptom" may be differentiated from "a sign" (e.g. clinical signs and clinical symptoms). However, for the purposes of this application, the term "symptoms" and "signs" are used interchangeably. Exemplary diseases that have symptoms associated with pathological protein aggregation are described above in Section I, and methods for diagnosing such diseases are known in the art. Exemplary symptoms associated with pathological protein aggregation may include impaired cognitive function, altered behavior, emotional dysregulation, seizures, and impaired nervous system structure or function. Impaired cognitive function includes but is not limited to difficulties with memory, attention, concentration, language, abstract thought, creativity, executive function, planning, and organization. Altered behavior includes but is not limited to physical or verbal aggression, impulsivity, decreased inhibition, apathy, decreased initiation, changes in personality, abuse of alcohol, tobacco or drugs, and other addiction-related behaviors. Emotional dysregulation includes but is not limited to depression, anxiety, mania, irritability, and emotional incontinence. Seizures include but are not limited to generalized tonic-clonic seizures, complex partial seizures, and non-epileptic, psychogenic seizures. Impaired nervous system structure or function includes but is not limited to hydrocephalus, Parkinsonism, sleep disorders, psychosis, impairment of balance and coordination. This includes motor impairments such as monoparesis, hemiparesis, tetraparesis, ataxia, ballismus and tremor. This also includes sensory loss or dysfunction including olfactory, tactile, gustatory, visual and auditory sensation. Furthermore, this includes autonomic nervous system impairments such as bowel and bladder dysfunction, sexual dysfunction, blood pressure and temperature dysregulation. Finally, this includes hormonal impairments attributable to dysfunction of the hypothalamus and pituitary gland such as deficiencies and dysregulation of growth hormone, thyroid stimulating hormone, lutenizing hormone, follicle stimulating hormone, gonadotropin releasing hormone, prolactin, and numerous other hormones and modulators.

In some embodiments, a symptom associated with pathological protein aggregation refers to dementia. Dementia is not itself a specific disease, but is an overall term that describes a wide range of symptoms associated with a decline in memory or other thinking skills severe enough to reduce a person's ability to perform everyday activities. Dementia is also shared clinical feature of many diseases associated with pathological protein aggregation. A skilled practitioner will be familiar with the numerous methods available to diagnose the severity of dementia. For example, several cognitive tests and screening questionnaires for dementia are known in the art, all with varying degrees of sensitivity and specificity. Non-limiting examples include the mini mental state examination (MMSE), the abbreviated mental test may score (AMTS), the modified mini mental state exam (3MS), the cognitive abilities screening instrument (CASI), the Trail-making test, the clock drawing test, the Informant Questionnaire on cognitive decline in the elderly, the General practitioner assessment of cognition, the Clinical Dementia Rating (CDR), Eight-item informant interview to differentiate aging and dementia (AD8).

In some embodiments, the severity of the symptoms of dementia are quantified using the CDR. Using the CDR, a score of 0 indicates no symptoms, a score of 0.5 indicates very mild symptoms, a score of 1 indicates mild symptoms, a score of 2 indicates moderate symptoms and a score of 3 indicates severe symptoms. Thus, any increase in a CDR score for a subject indicates a worsening in cognition and an increase in dementia. Moreover, change in CDR from 0 to greater than 0, indicates the development or onset of dementia.

The seeding activity of a sample may be measured by any method known in the art to detect one or more protein aggregates in a biological sample. In a preferred embodiment, a method as described in Section I is used. Subjects may be classified as having high or low seeding activity as measured in a biological sample obtained from said subject by using a cut-off value to discriminate high seeding activity from low seeding activity. Generally speaking, high seeding activity is a value above a cut-off value that discriminates a population of subjects without a symptom of pathological protein aggregation from a population of subjects with the symptom of pathological protein aggregation. A skilled artisan will appreciate that a value to discriminate high seeding activity from low seeding activity will depend upon the sample, the method used to measure the seeding activity and the type of symptom. For example, if seeding activity is measured by a method described in Section I above, seeding activity may be reported as fold-change in the detectable signal. The term "fold-change" refers to the relative induction of aggregation in a sample, as measured by the detectable signal. For example, if a sample has no seeding activity, the fold-change will be "1," indicating the sample value is identical to the control. A fold-change of "2" indicates that the sample doubled the baseline level of the detectable signal. An alternative readout could include complementation of luciferase activity, based on fusion of the N- and C-terminal halves of the luciferase enzyme to each aggregation-prone protein, or complementation of a split-green fluorescent protein. Other less-quantitative ways to monitor seeding activity could include visually inspecting cells for evidence of protein aggregation, as indicated by the formation of visible inclusions, or biochemical extraction of the cells to determine induction of detergent-insoluble material. Moreover, a cut-off value that discriminates a group of subjects with dementia from a group of subjects without dementia may be different than a cut-off value that discriminates a group of subjects with a different symptom from a group of subjects without that symptom.

A cut-off value may be identified by measuring the seeding activity in a collection of samples, wherein a high level is above the average and a low level is below the average. Alternatively, a cut-off value may be identified by measuring the seeding activity in two or more different collections of samples, determining the average seeding activity in each collection, and then using a statistical model to calculate a value that discriminates the collections. Seeding activity may be measured as described herein. In a preferred embodiment, seeding activity is measured using a cell-based system of the invention and measuring FRET by flow cytometry.

In embodiments where a multiple samples are collected from a subject over time and the tau seeding activity of the samples changes from low to high, (indicating a change from an absence of significant seeding to the presence of significant seeding), the subject may be within ten years of showing signs of dementia (e.g. converting from CDR<0 to CDR>0). For example, a subject may be within 1, within 2, within 3, within 4, within 5, within 6, within 7, within 8, within 9 or within 10 years of showing signs of dementia. Without being bound by theory, a skilled artisan will appreciate that the accuracy of such a prediction will depend greatly on when tau seeding activity was last measured. In an exemplary embodiment, a subject may be within 1 to 5 years of showing signs of dementia. In another exemplary embodiment, subject may be within 1 to 3 years of showing signs of dementia. In another exemplary embodiment, subject may be within 3 to 5 years of showing signs of dementia. In another exemplary embodiment, subject may be within 2 to 4 years of showing signs of dementia.

From the following description, one skilled in the art can easily ascertain comparable cut-off values using other methods suitable for determining an amount of protein aggregation known in the art and/or for other symptoms associated with pathological protein aggregation.

III. OTHER ASPECTS

A. Screen for Novel Antibodies and/or Small Molecule that Block Aggregate Uptake In another aspect, the invention encompasses a method to screen for novel antibodies and/or small molecules that block aggregate uptake using a biological sample. For example, a biological sample, (e.g. brain lysate, or aggregated proteins purified from brain), are added to a biosensor cell line of the invention to increase intracellular aggregation that is detected by FRET. This approach could be used to screen for antibodies that would block "seeding," i.e. induction of intracellular aggregation by exogenous fibrils, or it could be used to screen for small molecules that would block seeding. Such molecules (antibodies or small molecules) could be blocking protein aggregates from binding the cell surface, preventing their uptake into cells, or preventing subsequent intracellular seeding. In some embodiments, a single biological sample is used. In other embodiments, multiple biological samples are pooled together. In embodiments where a single biological sample is used, the method of invention may be used to tailor a treatment decisions to that particular subject. Stated another way, a method of the invention may be used to identify in advance of treatment which antibody or compound will be the most effective for a subject based on whether the antibody or compound reduces the seeding activity in the subject's biological sample. If the seeding activity is reduced, the compound may be effective. If the seeding activity is not reduced or increases, the compound is not effective.

B. Identify Genes Involved in Aggregate Uptake

In another aspect, the invention encompasses a method to identify genes involved in aggregate uptake. For example, knockdown or overexpression of candidate genes within the biosensor cell line of the invention would allow identification of genes involved with aggregate uptake into cells and subsequent seeding. This could enable identification of potent drug targets for chemical inhibition.

In some embodiments, a gene involved in aggregate uptake may encode a cell surface receptor. In other embodiments, a gene involved in aggregate uptake may encode a protein involved in the synthesis of a cell surface receptor. For example, the Applicants have recently identified heparan sulfate proteoglycans (HSPGs) as a cell surface receptor for aggregated tau and alpha-synuclein. HSPGs are comprised of a core protein that is modified with at least one heparan sulfate chain. Many different cell types produce heparan sulfate chains with many different primary structures. Therefore, there is a great deal of variability in the way heparan sulfate chains are synthesised. However, essential to the formation of HS regardless of primary sequence is a range of biosynthetic enzymes. These enzymes consist of multiple glycosyltransferases, sulfotransferases and an epimerase. In embodiments where the cell surface receptor is a heparan sulfate proteoglycans, genes encoding heparan sulfate proteoglycans may refer to proteins involved in the chain initiation, chain elongation, chain modification, N-deacteylation, N-sulfation, 6-O-sulfation, 3-O-sulfation.

IV. DEFINITIONS

The term "aggregation-prone domain" refers to a region of the amino acid sequence of a protein that promotes the protein's aggregation.

The term "protein", includes peptides, polypeptides, fusion proteins, naturally occurring proteins, recombinant or artificially synthesized proteins, and analogs, fragments, derivatives or combinations thereof. The term "naturally occurring protein" refers to a protein that is encoded by a nucleic acid sequence that is typically present in the wild-type genome of the cell expressing it. The term "recombinant protein" refers to a protein that is encoded by a nucleic acid sequence that is not typically present in the wild-type genome of the cell expressing it.

A "seed" refers to one or more proteins that nucleate aggregation of other proteins with a similar aggregation domain. The "seeding activity" of a sample refers to the ability of a sample to nucleate (i.e. induce) aggregation of a protein with a similar aggregation domain as measured in vitro. The protein may or may not be a pathological protein. Typically, the seeding activity of a sample increases as the amount of protein aggregate in the sample increases.

EXAMPLES

The following examples illustrate various iterations of the invention.

Example 1. Seeding Assay Detects Aggregates Present in Alzheimer Brain

Figure 2:
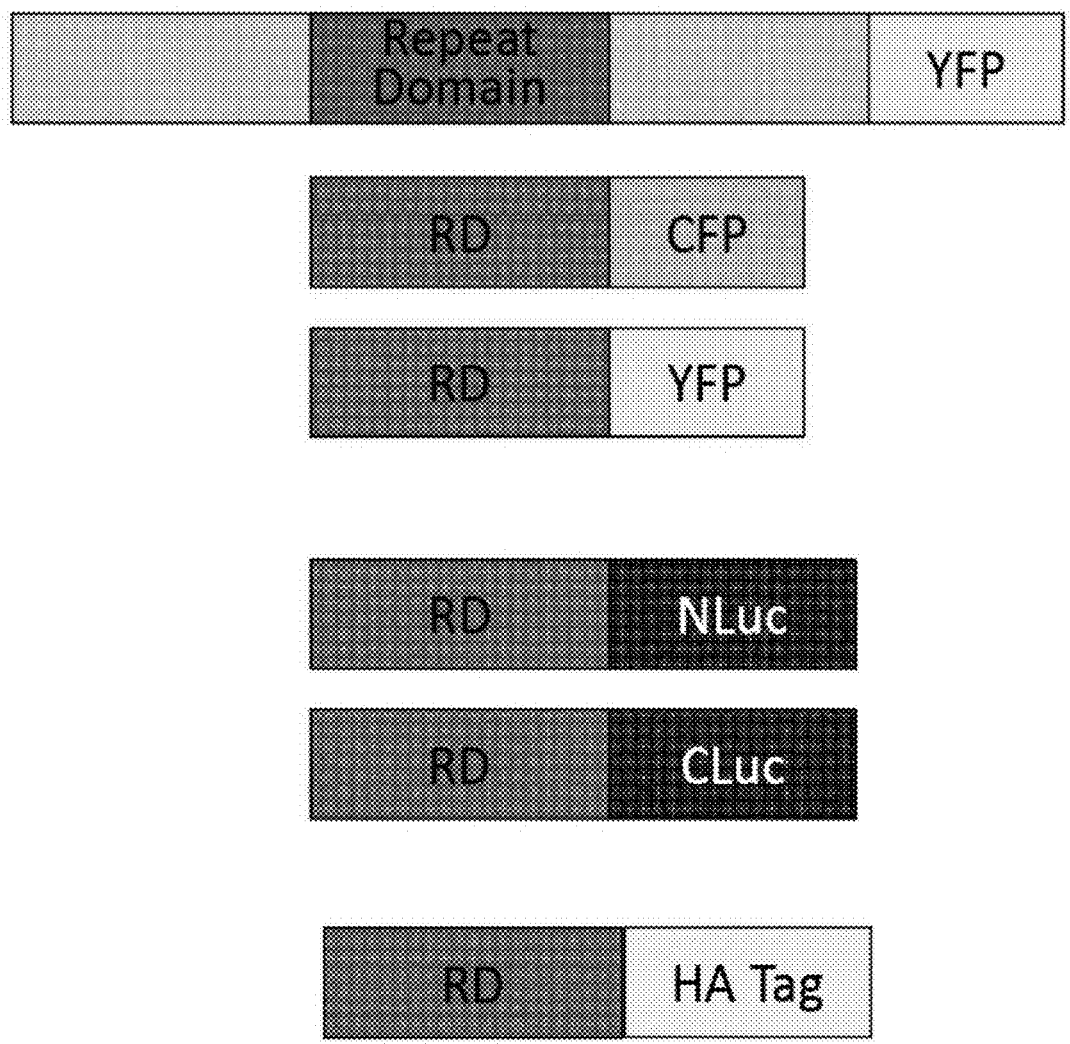
FIG. 2 depicts drawings of reporter constructs used to detect aggregation of tau proteins. In (A), full-length tau protein (2N, 4R) is fused to YFP. In (B), the repeat domain (RD), which is the aggregation-prone core of the protein, is fused to CFP or YFP for aggregate detection by FRET. In (C), the RD is fused to split click beetle luciferase (NLuc or CLuc) for aggregate detection via enzyme complementation and luminescent signal.
Figure 3:
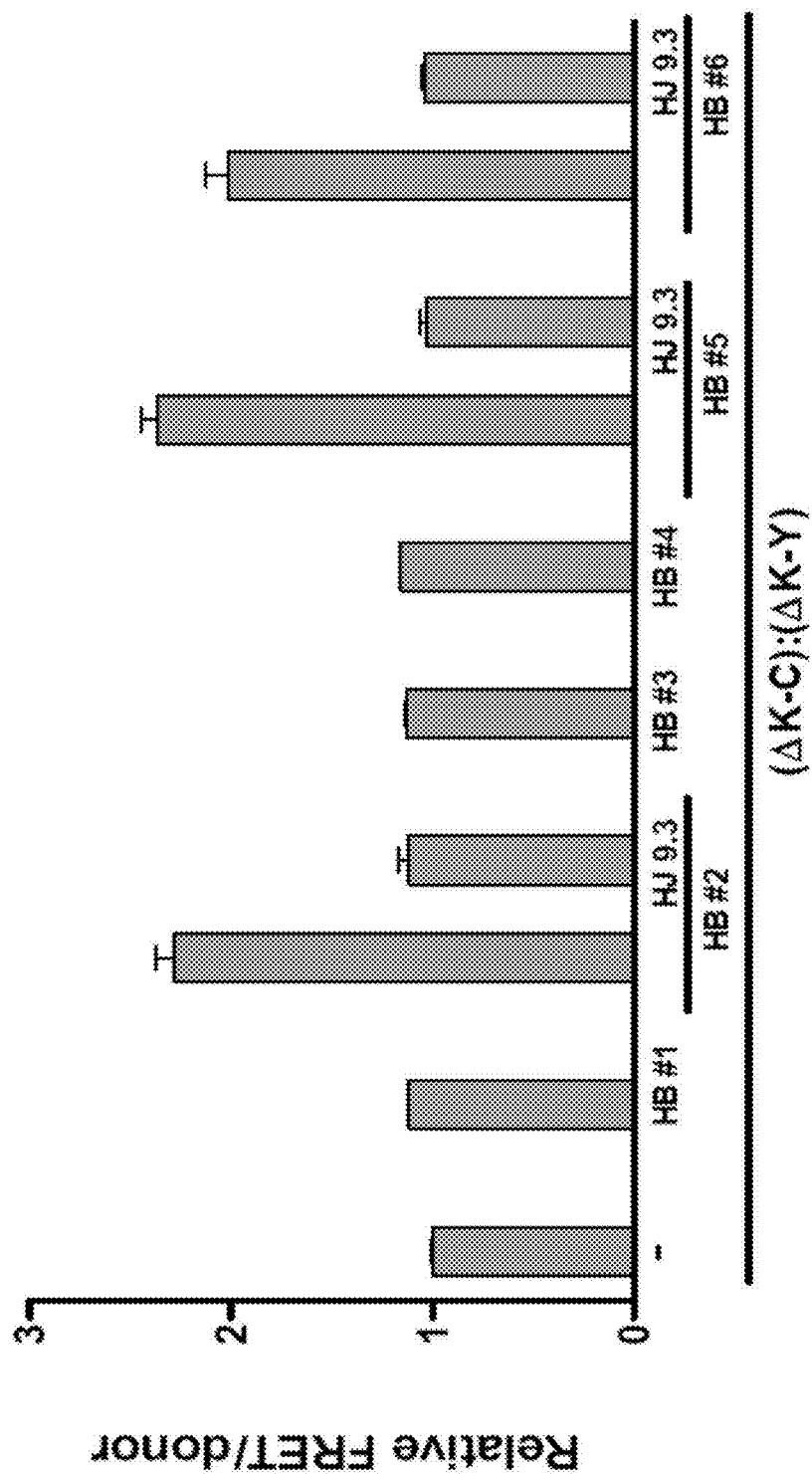
FIG. 3 depicts a bar graph showing tau seeding activity in human brain (HB) lysates from AD patients but not that of normal patients. An increase in FRET signal corresponds to an induction of endogenous tau aggregation by seeds present in the lysates. Description of human samples along the X-axis: (-) buffer alone; HB #1=normal; HB #2=AD (CRD 3.0); HB #3=normal patient; HB #4=AD (CDR 0); HB #5=AD (CDR 0); HB #6=AD (CDR 3.0). Samples HB #1, HB #3, and HB #4 did not induce aggregation relative to the control (-). Samples HB #2, HB #5, and HB #6 did induce aggregation (left bar graph); immunodepletion of tau using HJ9.3 anti-tau monoclonal antibody eliminated the seeding activity (right bar graph). Technical replicates: n=3 for each; error bars represent the SEM.

HEK293 cells were co-transfected with tau repeat domain (RD) fused to cyan and yellow fluorescent protein: RD-CFP or RD-YFP (FIG. 2B). HEK293 cells expressing RD(ΔK)-CFP/YFP were exposed to 1:24 dilution of crude brain lysates for 24 h. Brain lysates collected from human Alzheimer Disease (AD) patients (CDR 0 or 3.0) or healthy controls were added to cells for 24 hours and the FRET signal was measured. As shown in FIG. 3, brain lysates collected from AD patients induced aggregation of RD(ΔK)-CFP/YFP but brain lysates collected from normal patients did not. Samples that induced aggregation were then immunodepleted of tau using HJ9.3 anti-tau monoclonal antibody. Immunodepletion of tau eliminated the seeding activity. (AD patients n=4, normal patients n=2, technical replicates n=3 for each, error bars represent the SEM).

Figure 4:
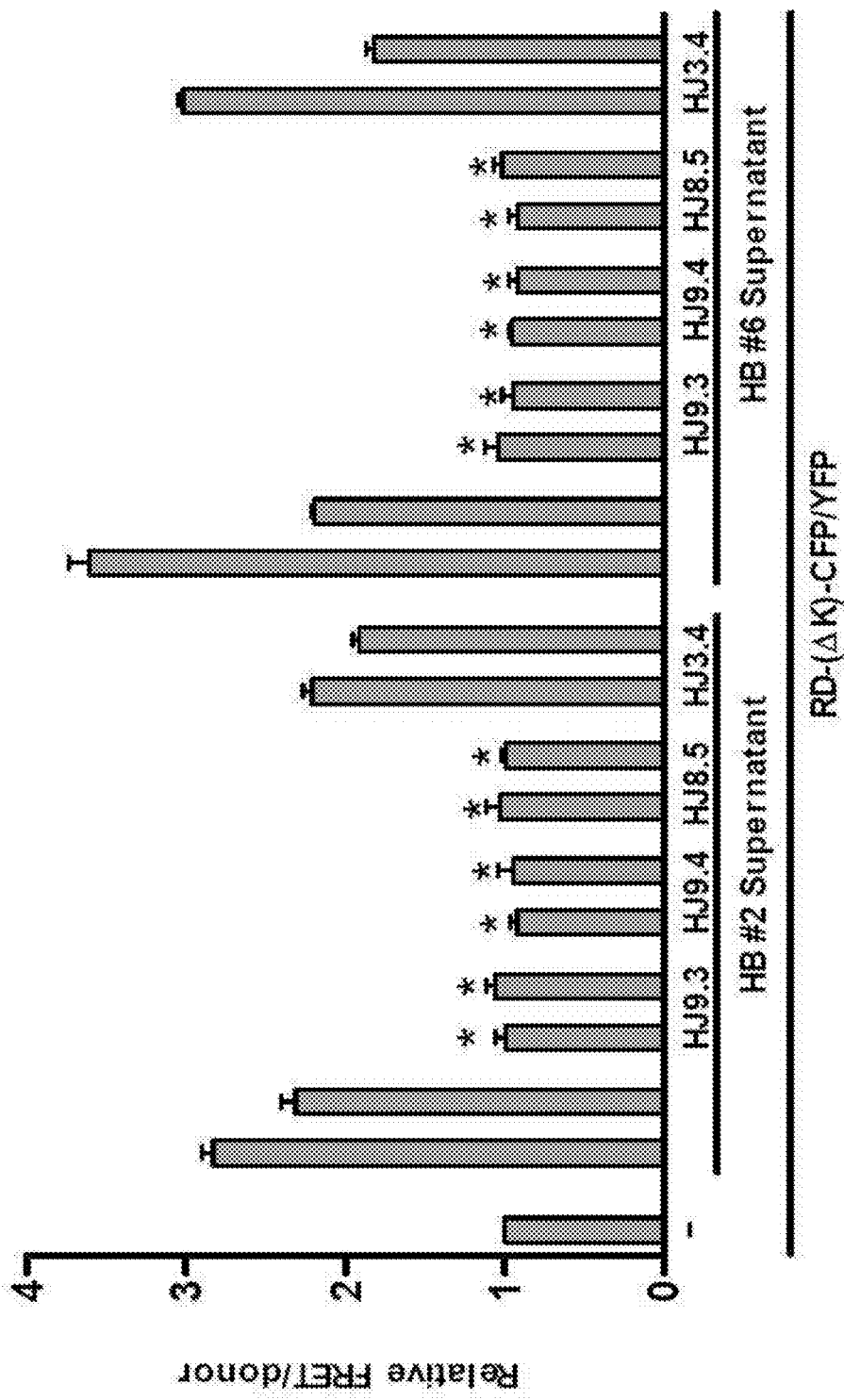
FIG. 4 depicts a bar graph showing tau seeding activity in human brain (HB) lysates can be depleted by anti-tau monoclonal antibodies. Lysates from two AD patients were incubated with no antibody (bar graphs with no label) or with antibody at 4° C. overnight, supernatants were collected (HB #2 supernatant and HB #6 supernatant) and 1:80 dilutions were exposed to HEK293 cells expressing RD(ΔK)-CFP/YFP for 24 hours and a FRET signal was measured. An increase in FRET signal corresponds to an induction of endogenous tau aggregation by seeds present in the samples. Two technical replicates are shown for each experimental condition, except for buffer alone (-). HJ9.3, HJ9.4 and HJ8.5 are anti-tau monoclonal antibodies. HJ3.4 is an anti amyloid-β monoclonal antibody. * indicates a p-value <0.0001; error bars represent the SEM. Relative FRET/donor refers to the amount of FRET signal induced by a given sample. For example, a value of "1" indicates no change, or no seeding activity, "2" indicates a 2-fold, or 100% increase in signal induced by the sample.

Example 2. Antigen/Antibody Clearance Assay: Screening for Anti-Seeding Antibody Activity To further demonstrate the specificity of the seeding assay, the ability of anti-tau antibodies to deplete the seeding activity of human AD brain lysates was compared to an anti-amyloid-beta (aβ) antibody. Brain lysates collected from human AD patients were incubated with anti-tau monoclonal antibodies (HJ9.3, HJ9.4, HJ8.5) or a control anti-aβ monoclonal antibody (HJ3.4) at 4 C overnight, and then antigen/antibody complexes were pulled down with protein-G-agarose beads. HEK293 cells expressing RD(ΔK)-CFP/YFP were then exposed to a 1:80 dilution of human AD brain lysates or immunodepleted brain lysates for 24 h. As shown previously, brain lysates collected from AD patients induced aggregation of RD(ΔK)-CFP/YFP but not from antigen/anti-tau antibody depleted AD brain lysates (FIG. 4; * indicates a p-value <0.0001, error bars represent the SEM). Anti-aβ antibody did not significantly reduce the seeding activity of AD brain lysates. This confirms the presence of tau "seeds" in the human AD brain lysates and demonstrates that the assay may used to screen for antibodies that interfere with or deplete the seeding activity of biological samples.

Figure 5A:
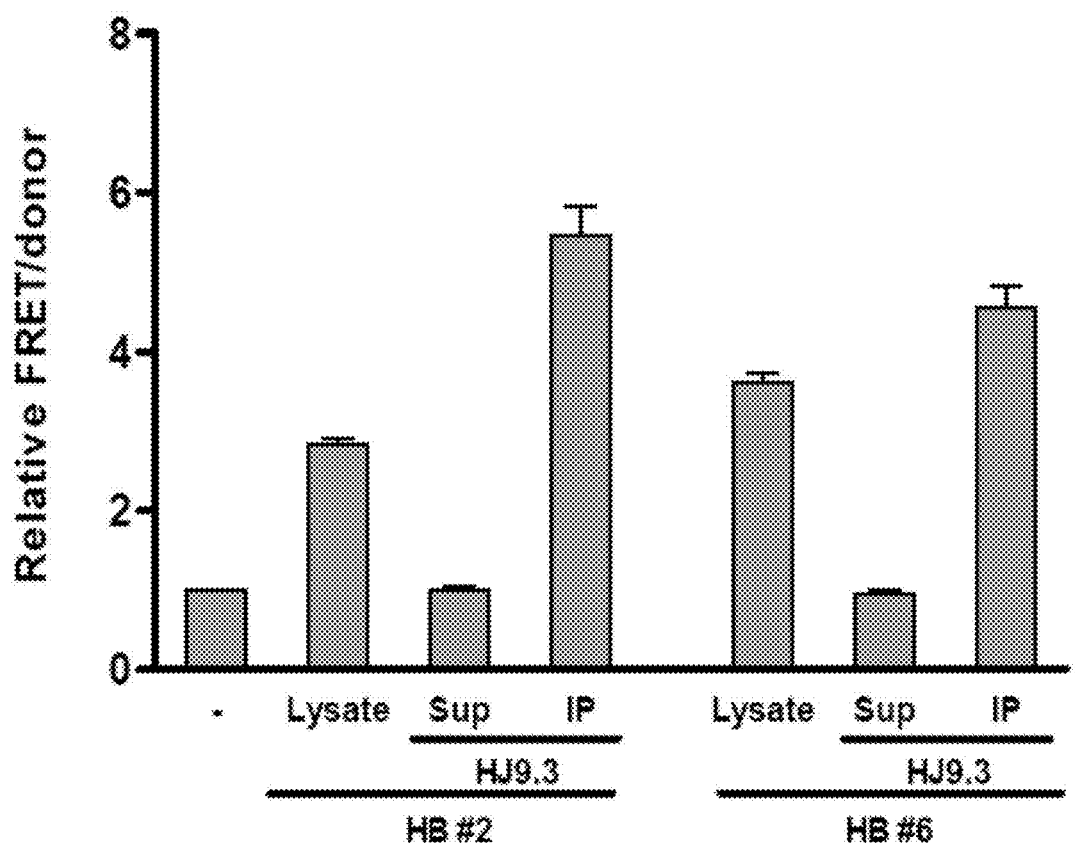
FIG. 5 depicts a bar graph showing human brain (HB) lysates contain transmissible tau seeds that can be immunoprecipitated with a tau-specific antibody. Lysates from two AD patients (HB #2 and HB #6) were incubated with antibody at 4° C. overnight, and supernatant (Sup) and immunoprecipitated tau seeds (IP) were collected. HEK293 cells expressing RD(ΔK)-CFP/YFP were exposed to 1:80 dilutions of HB lysate (Lysate), Sup and IP for 24 hours and FRET signal was measured. An increase in FRET signal corresponds to an induction of endogenous tau aggregation by seeds present in the sample. Error bars represent the SEM. In (A) the antibody is HJ9.3. In (B) the antibody is HJ3.4.
Figure 5B:
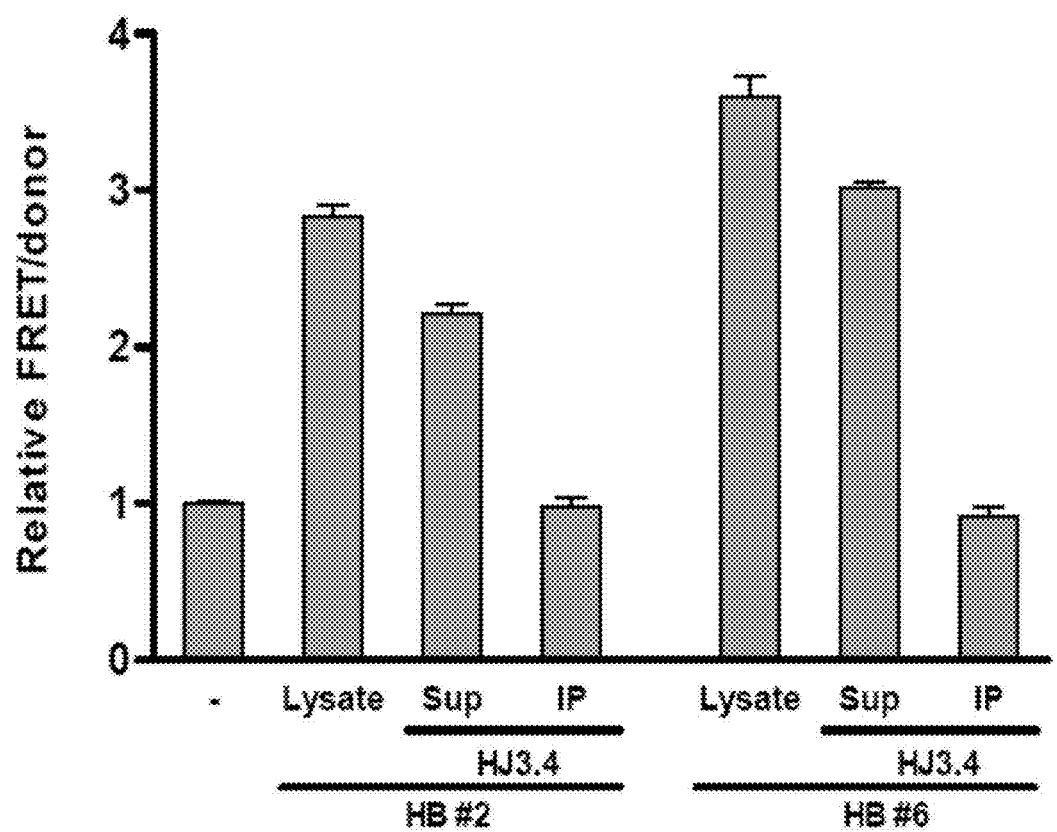

Example 3. Immunoprecipitates of AD Human Brain Lysates Contain Transmissible Tau Seeds To confirm that the assay has the sensitivity to measure aggregation induced by tau seeds purified from a biological sample (e.g. does not require other components of the biological sample, HEK293 cells expressing RD(ΔK)-CFP/YFP were exposed for 24 hours to 1:80 dilutions of human AD brain lysates, tau-depleted brain lysates or tau seeds immunoprecipitated (IP) from human AD brain lysates. Lysates collected from AD patients induced aggregation of RD(ΔK)-CFP/YFP. Depletion of the lysates with a tau-specific antibody (HJ9.3; FIG. 5A) blocked the effects of the lysates. Non-specific antibody (HJ3.4; FIG. 5B) had no effect. Reapplication of tau seeds immunoprecipitated using HJ9.3 (FIG. 5A), but not HJ3.4 (FIG. 5B), further induced aggregation of RD(ΔK)-CFP/YFP. These results demonstrate that the assay is sensitive to tau seeds.

Example 4. Tau Seeding Activity in Transgenic Tau Mice

Figure 6A:
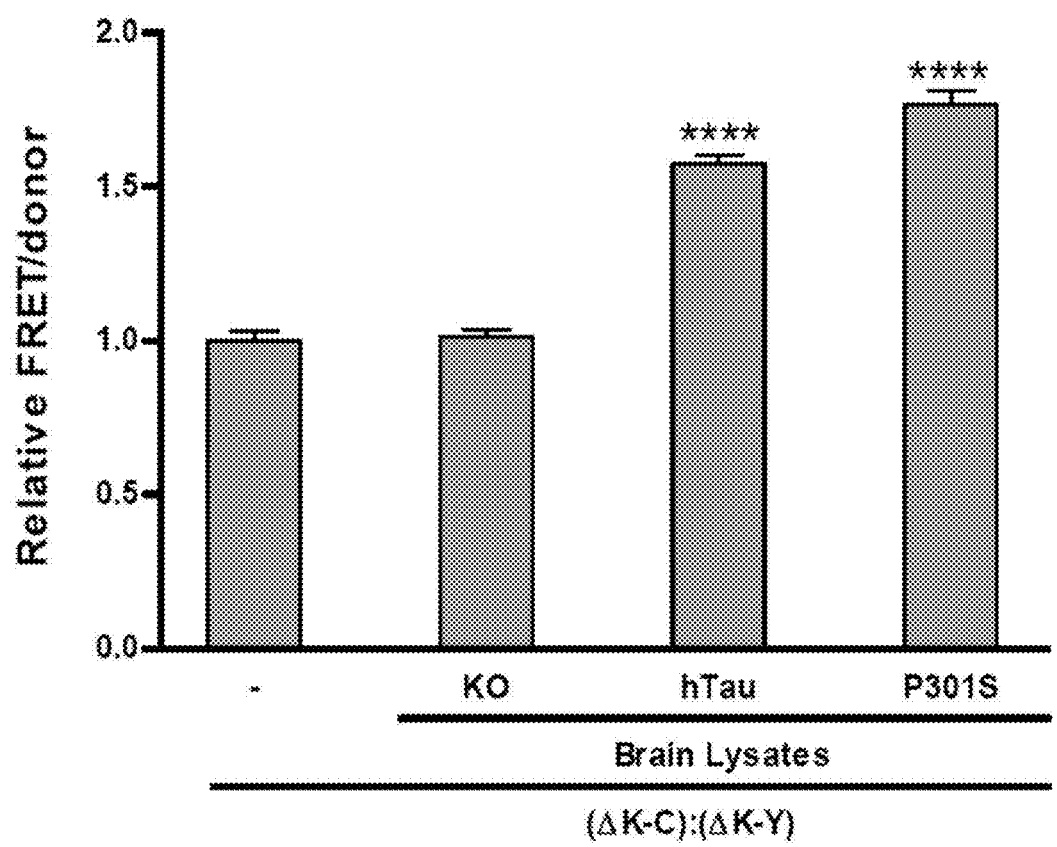
FIG. 6 depicts a bar graph (A) and a dot plot (B) showing tau seeding activity in brain lysates from 12-month old transgenic tau mice (hTau and P301S) or tau knockout (KO) mice. HEK293 cells expressing RD(ΔK)-CFP/YFP were exposed to 1:24 dilutions of crude brain for 24 hours and a FRET signal was measured. An increase in FRET signal corresponds to an induction of endogenous tau aggregation by seeds present in the lysates. Brain lysates collected from hTau and P301S mice induced aggregation of RD(ΔK)-CFP/YFP (n=4 and n=5 respectively) but not lysates from knockout (KO) mice (n=7), or buffer alone (-). (**** indicates a p-value <0.0001, error bars represent the SEM).
Figure 6B:
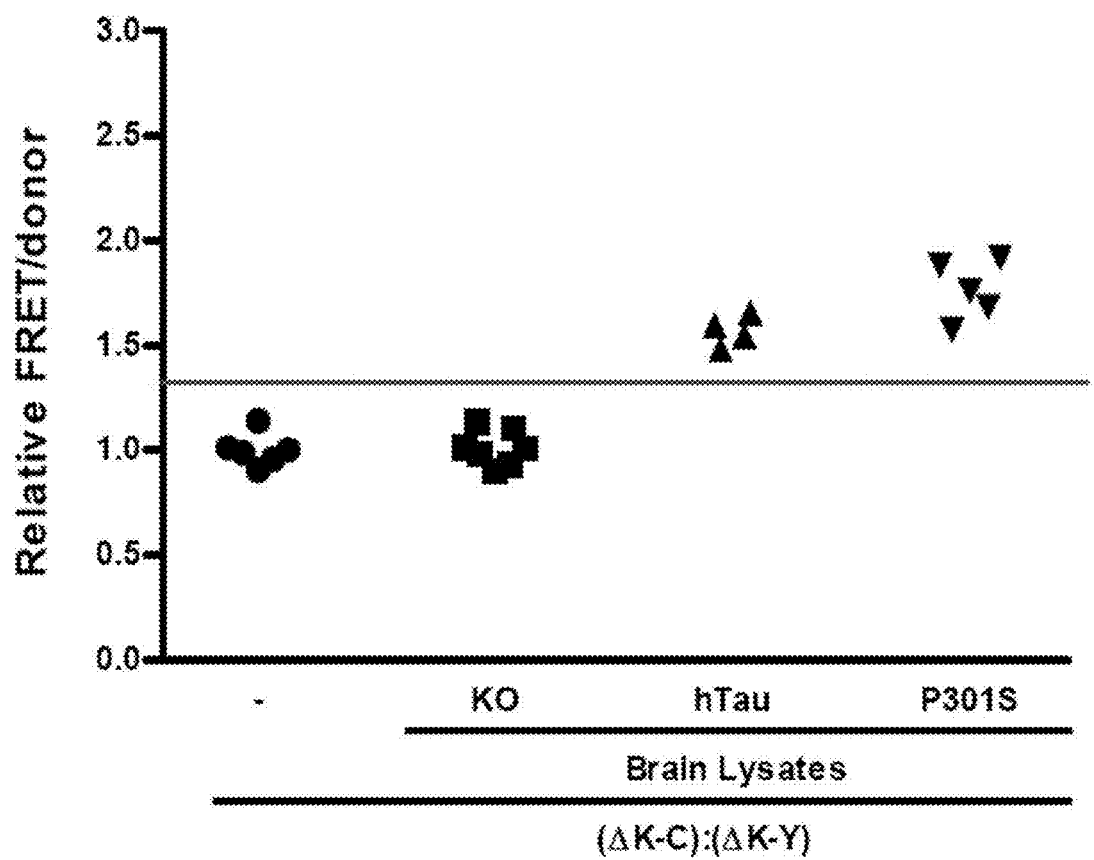
Figure 7:
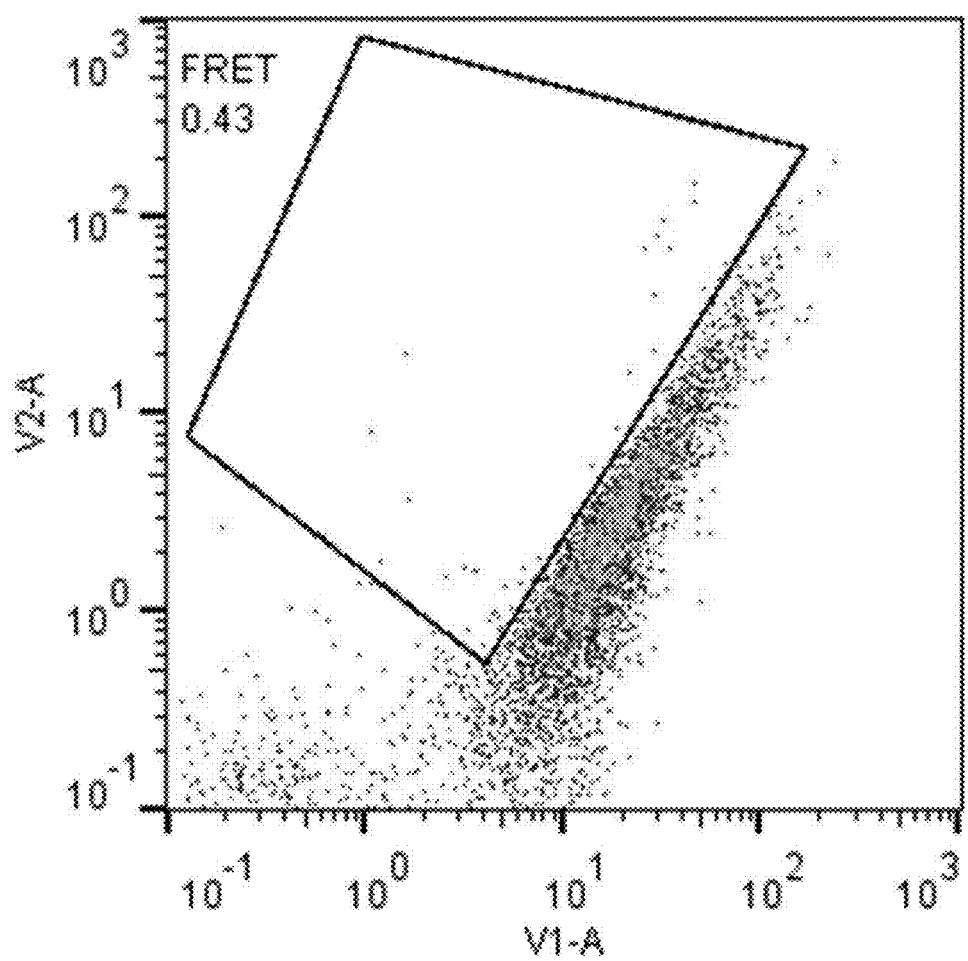
FIG. 7 depicts a fluorescence bi-variate plot of the fluorescence detected by flow cytometry for a population of FRET negative cells. The y-axis (V2-A) is the FRET channel and the x-axis (V1-A) is the donor channel. Biosensor cells were treated with vehicle only. The gate (indicated by the box) has been chosen to exclude ~99.5% of cells and is positioned to detect FRET positive cells as they shift in the vector illustrated by the red arrow.
Figure 8:
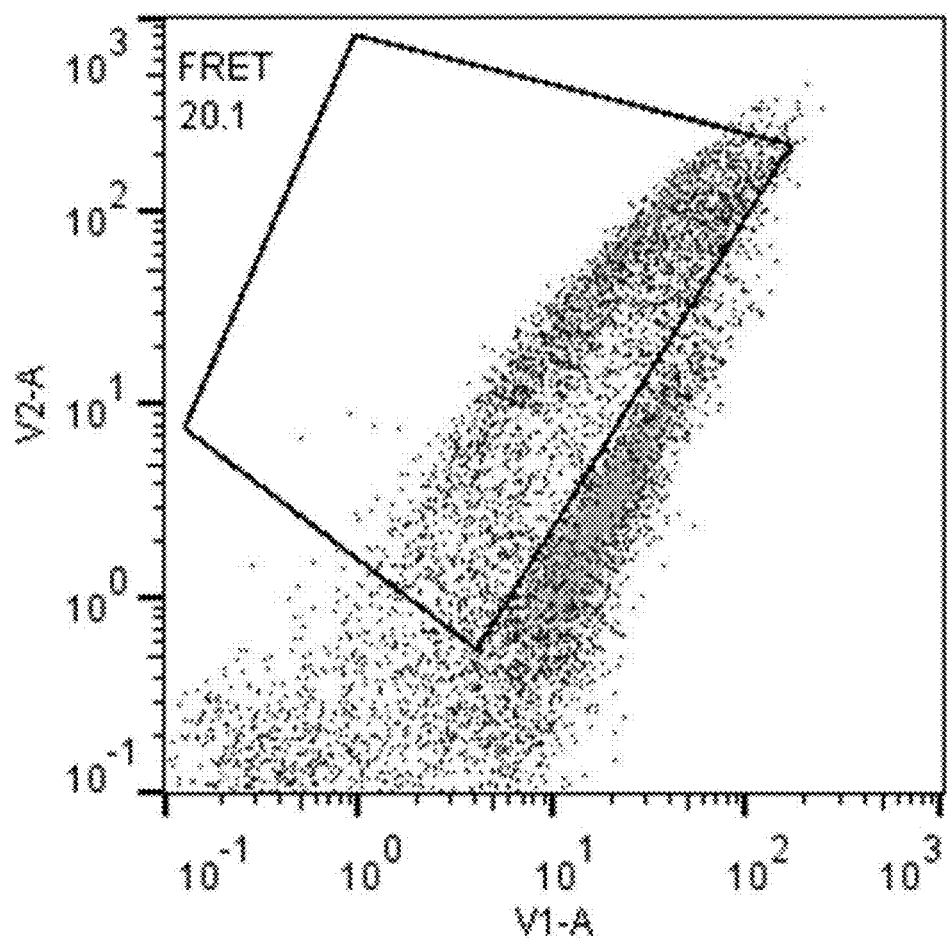
FIG. 8 depicts a fluorescence bi-variate plot of the fluorescence detected by flow cytometry for a population of FRET cells treated with recombinant tau aggregates. The y-axis (V2-A) is the FRET channel and the x-axis (V1-A) is the donor channel. Biosensor cells were treated with recombinant tau aggregates (100 nM) for 48 hours. The cells in the gate represent FRET positive cells. Of note, a similar percentage of cells show visible fluorescent puncta (aggregates) when visualized by microscopy (i.e., the flow cytometer is reading out a FRET signal that corresponds to what is observed by eye).
Figure 9:
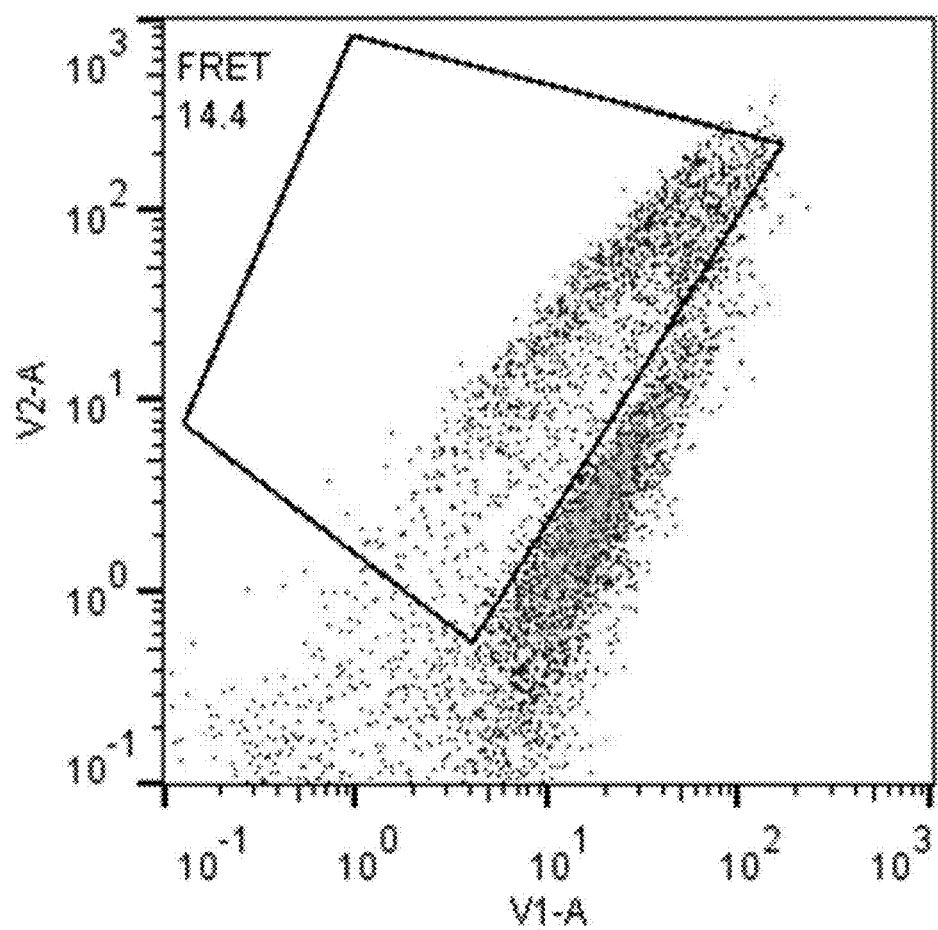
FIG. 9 depicts a fluorescence bi-variate plot of the fluorescence detected by flow cytometry for a population of FRET cells treated with recombinant tau aggregates. The y-axis (V2-A) is the FRET channel and the x-axis (V1-A) is the donor channel. Biosensor cells were treated with recombinant tau aggregates (10 nM) for 48 hours. The cells in the gate represent FRET positive cells. Of note, a similar percentage of cells show visible fluorescent puncta (aggregates) when visualized by microscopy (i.e., the flow cytometer is reading out a FRET signal that corresponds to what is observed by eye).

To further confirm the sensitivity and specificity of the seeding assay, aggregation induced from biological samples of transgenic (tg) mice expressing a human tau isoform were tested. Brain lysates, CSF and serum were collected from 12-month old transgenic mice: hTau mice that over-express all six isoforms of human tau and which develop progressive neuropathology, P301S tg mice, which overexpress P301S human T34 isoform tau (1N4R) on a B6C3 background, and tau knock-out mice. HEK293 cells expressing RD(ΔK)-CFP/YFP were exposed to 1:24 dilution of crude brain lysates for 24 hours. Brain lysates collected from hTau and P301S mice induced aggregation of RD(ΔK)-CFP/YFP (n=4 and n=5 respectively) but not lysates from knockout (KO) mice (n=7), or buffer alone (-) (FIG. 6, **** indicates a p-value <0.0001, error bars represent the SEM). These data show induction of endogenous tau aggregation by seeds present in brain lysates from hTau and P301S mice but not from knockout mice.

Example 5. Detection by Flow Cytometry

In order to increase the dynamic range of the assay, detectable signal was also measured by flow cytometry. Using a flow cytometery, the dynamic range increased dramatically and also provided higher sensitivity, precision and the ability to look at aggregation state at the single cell level. See FIGS. 7-9 and FIGS. 13-14. In particular, note a 3-fold response in FRET can be seen at 125 pM when FRET flow cytometry is used and the dynamic range of transfected cells spans ~100 fold above background.

Figure 14:
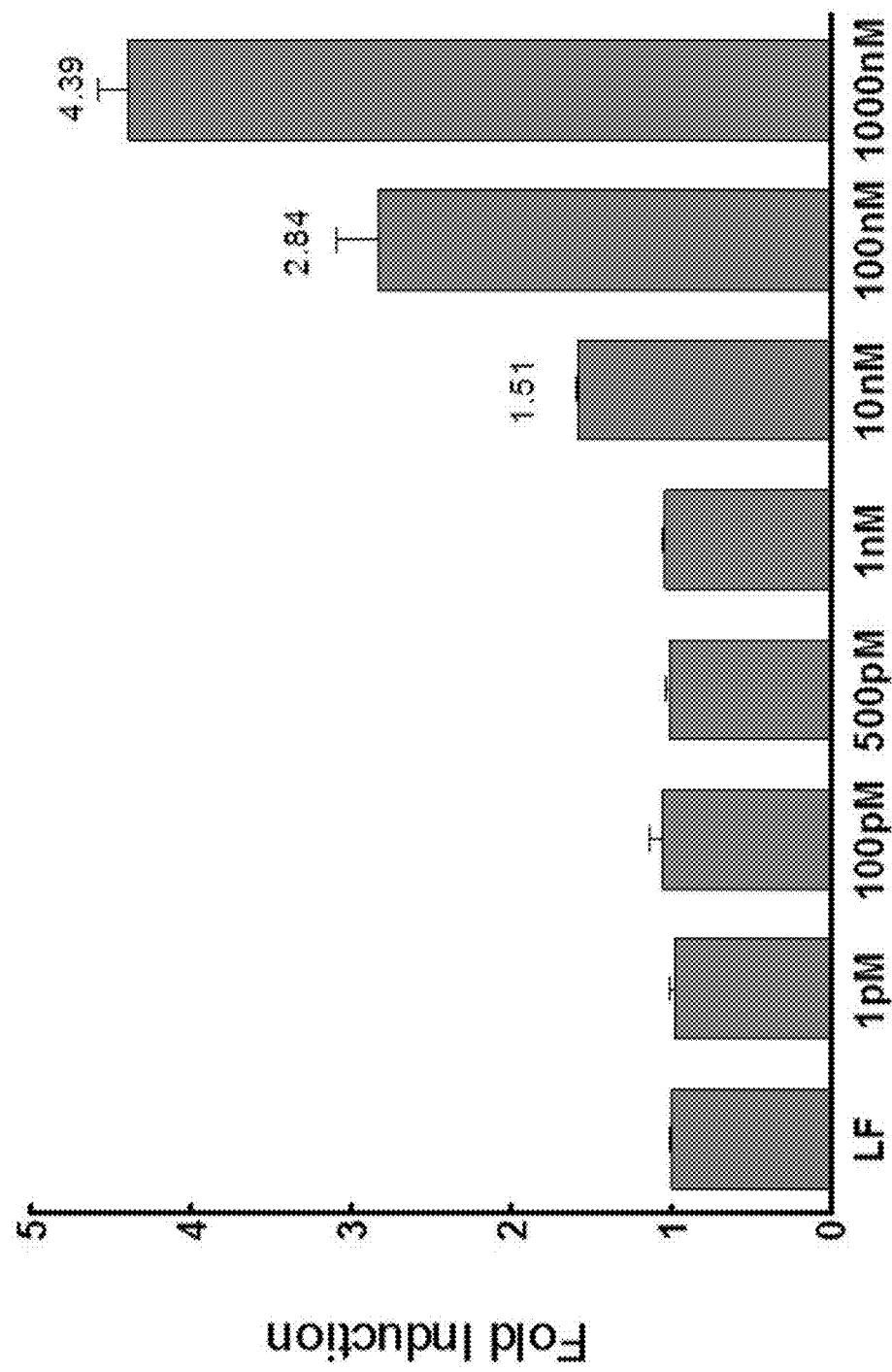
FIG. 14 shows a bar graph depicting the sensitivity and range of the biosensor cells when the detectable signal is measured by a Tecan plate reader. HEK293 cells were transfected with tau RD P301S. Tau RD fibrils were applied to them for 24 hours at different doses. By comparison to FIG. 13, note that changes in FRET are not observed until much higher concentrations and the dynamic range is significantly smaller. The y-axis is the fold induction. The x-axis is tau fibril concentration (pM).
Figure 15:
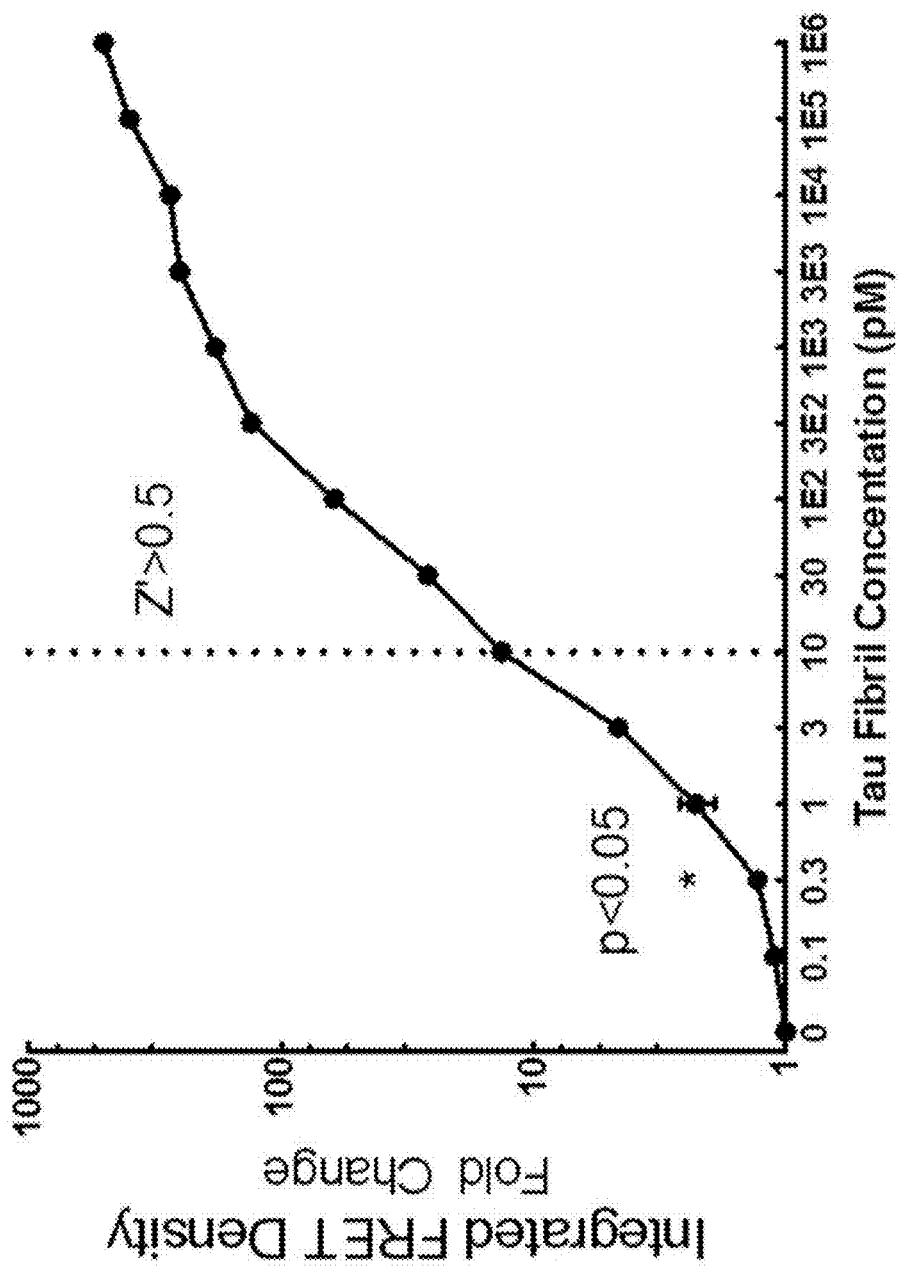
FIG. 15 depicts a graph showing sensitivity of the tau RD P301S monoclonal stable line. Experimental design is similar as that described in FIG. 13, with the exception of the cell line used. In this experiment, the tau RD P301S monoclonal stable line was used. This biosensor can reliably detect tau at 316 fM (p=0.0368) and has a dynamic range of ~500 fold over background. The dotted line represented the concentration at which the Z factor breaches 0.5. The y-axis is the fold change in integrated FRET density (integrated FRET density is the product of percent positive cells and median FRET intensity). The x-axis is tau fibril concentration (pM).
Figure 16:
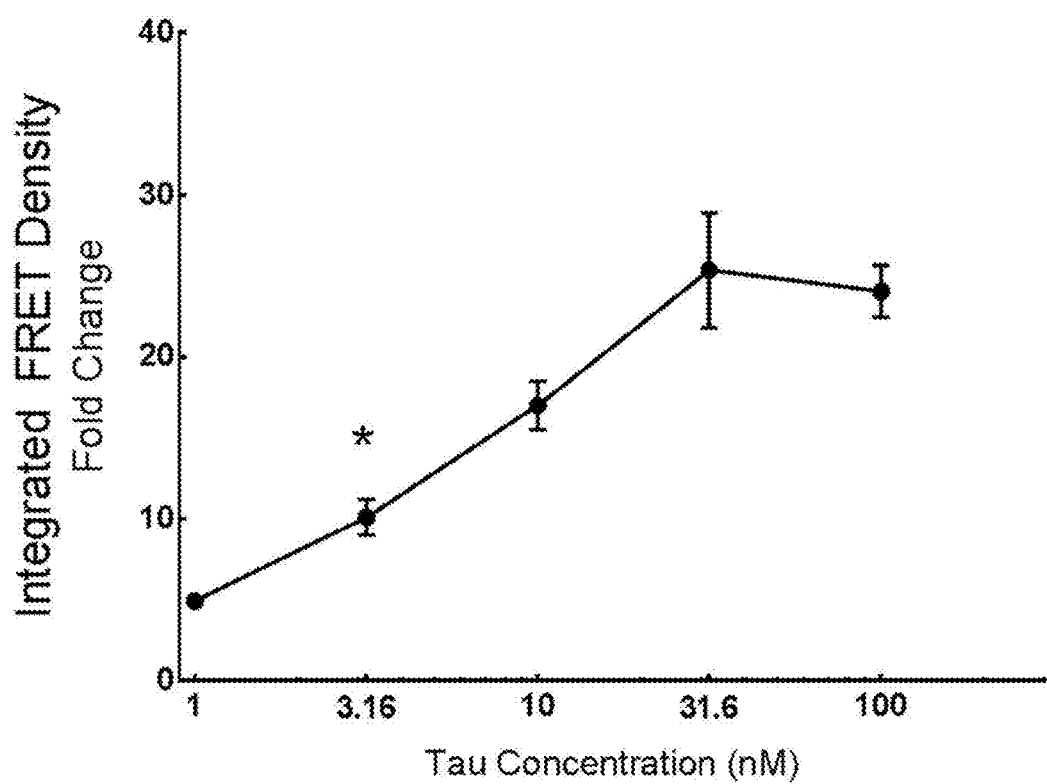
FIG. 16 depicts a graph showing detection of tau seeds in primary neurons. This experiment demonstrates that FRET flow cytometry can be used to detect seeding activity in primary hippocampal neurons and without the use of lipofectamine 2000. In other words, this experiment demonstrates that this system can query neuronal biology and not just serve as a diagnostic assay. Primary hippocampal neurons from WT E18.5 embryos were dissected and plated. At DIV 0 (days in vitro), the neurons were treated with tau RD P301S CFP and tau RD P301S YFP lentivirus. At DIV 4, cells were treated with recombinant tau fibrils without the use of lipofectamine. Thus, the fibrils entered the neurons via native uptake mechanisms. At DIV 7, the neurons were harvested for flow cytometry. The flow cytometry, gating, and analysis was conducted as previously described. The y-axis is the fold change in integrated FRET density (integrated FRET density is the product of percent positive cells and median FRET intensity). The x-axis is tau concentration (nM).
Figure 17:
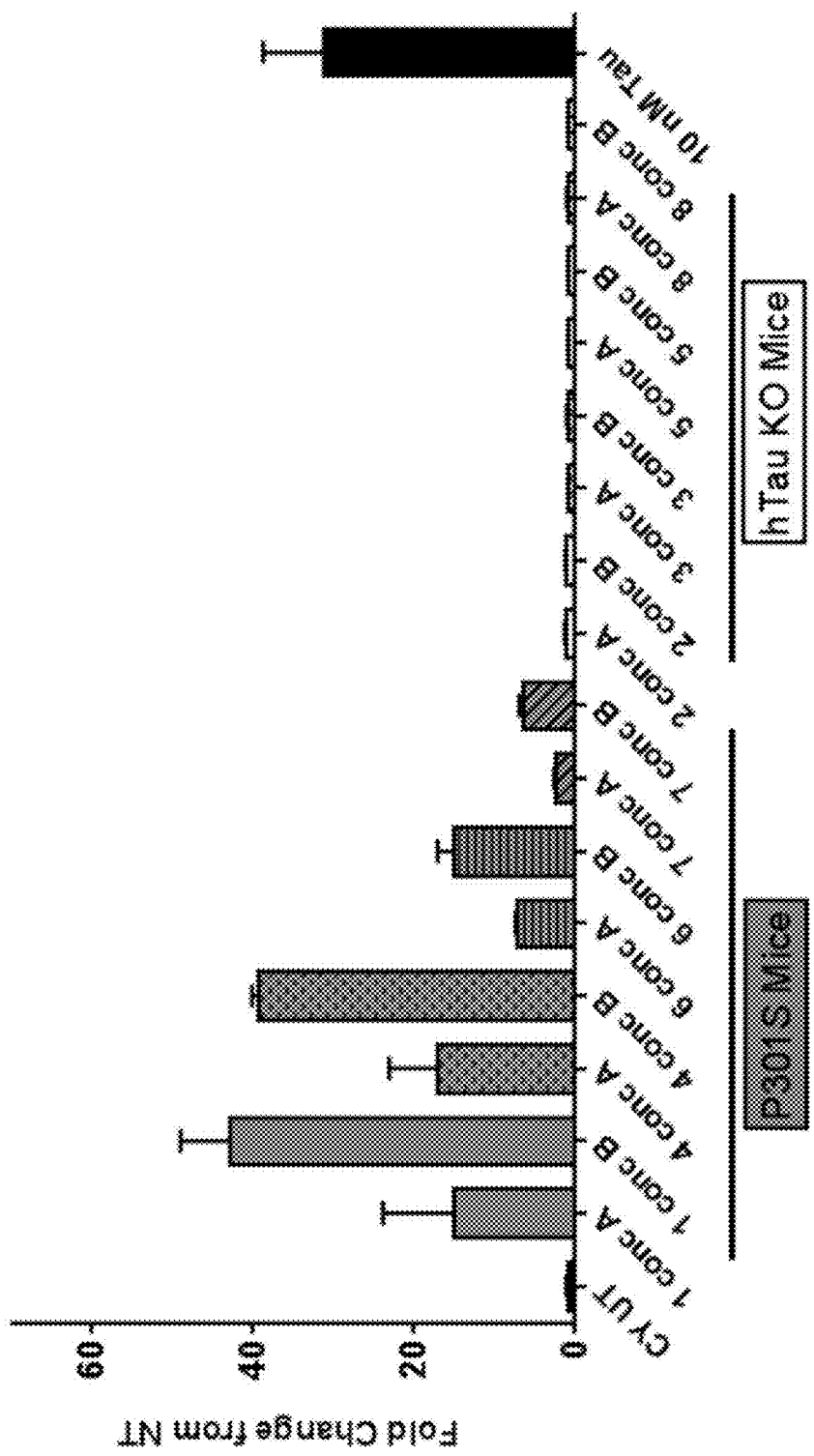
FIG. 17 depicts a graph showing the P301S monoclonal line is a reliable biosensor of seeding from brian lysates. Using the P301S monoclonal biosensor line, brain lysate from 1 yr old P301S mice was transduced for 24 hours. Mouse 1, 4, 6, and 7, showed a robust seeding response. Mouse 2, 3, 5, and 8 were tau knockout mice and gave no FRET response. Concentration A=1 uL and concentration B=2 uL. The lysates were made by homogenizing them at 10× volume over weight in TBS with protease inhibitor.
Figure 18:
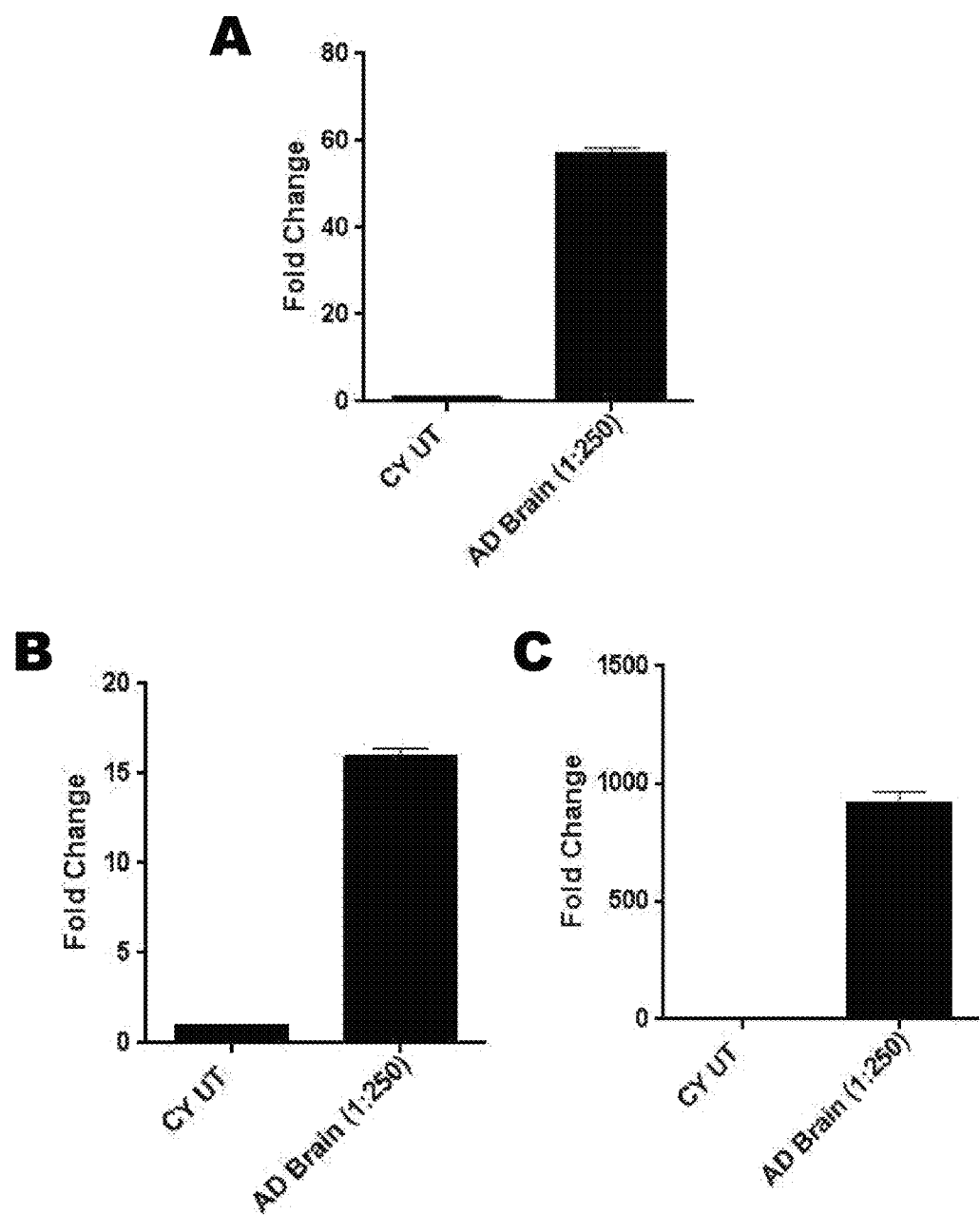
FIG. 18 depicts graphs showing the P301S monoclonal line is a reliable biosensor of seeding from brian lysates. Using the P301S monoclonal biosensor line, brain lysate from human subjects with Alzheimer's Disease was transduced for 24 hours. Control cells were treated with lipofectamine only. In (A), data is expressed as Fold Change in % Positive Total. In (B), data is expressed as Fold Change in Mean FRET Intensity. In (C), data is expressed as Fold Change in Integrated FRET Density.

FIGS. 14 and 15 show detection by flow cytometry using a stable monoclonal line. Lentivirus vectors were used to stably transfect HEK293 cells with genes to express tau RD (P301S)-CFP or tau RD (P301S)-YFP. The cells were cultured for 2 weeks, and then sorted using FACS to identify a sub-population of cells with RD-CFP/YFP expression levels suitable for FRET assays. Cells were plated to a limiting dilution on a 10 cm plate, and individual clones were isolated and cultured. These were subsequently expanded and analyzed to find the ones with the most robust signal/noise ratio.

This tau aggregation "biosensor" line was subsequently used to characterize seeding activity from recombinant fibrils and brain tissue lysates, as demonstrated in FIG. 13-18. The tau RD P301S monoclonal line is cultured such that the cells are 70% confluent at the time of treatment. Tau seeds (either recombinant or brain derived) are transduced into the monoclonal line via Lipofectamine 2000. 24-hours post transduction the cells are harvested for flow cytometry. FRET measurements are performed using a VYB (Miltenyi) equipped with a 405 nm, 488 nm and 561 nm lasers. To measure CFP and FRET, cells are excited with the 405 nm laser and CFP fluorescence is collected with a 450/50 filter while the FRET signal is captured with the 525/50 filter. To measure YFP, cells are excited with the 488 nm laser and fluorescence is also captured with the 525/50 filter. "False FRET" arising from YFP emission into the FRET-channel is eliminated via an exclusion gate from control cells expressing YFP-tau RD only. For each sample, a minimum of 20,000 cells are evaluated.

Example 7. Huntingtin Seeding Activity

Figure 10:
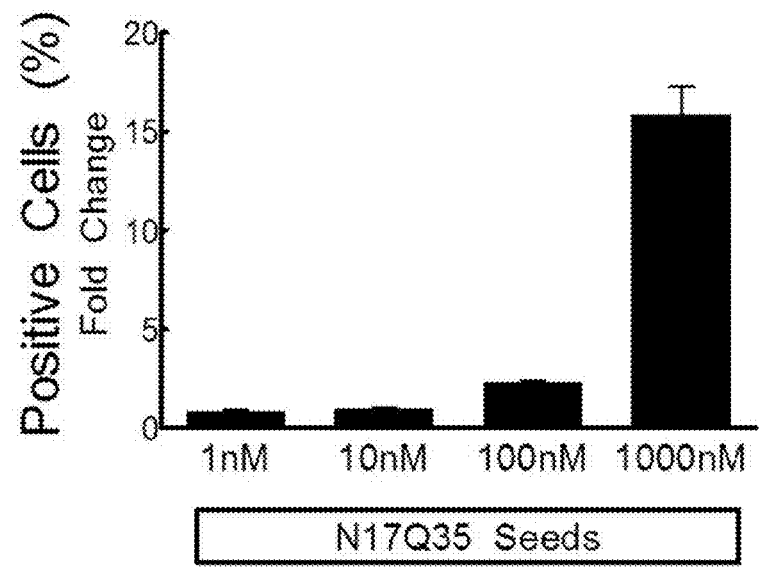
FIG. 10 depicts a graph showing the huntingtin biosensor cell line can detect N17Q35 in a dose dependent manner. HEK293 cells were transiently transfected with exon 1 of Huntingtin with a glutamine expansion of 25 residues (Htt$_{Exon1}$Q25) fused to a CFP and a YFP variant. 24 hours after transfection cells were treated with synthetic N17Q35 (first 17 amino acids of Htt followed by 35 glutamines) for 24 hours. The cells were then harvested for flow cytometry and analyzed for FRET positivity as described for the tau biosensor cell line. The y-axis is the fold change in percent positive cells (percent positive cells is the percentage of cells that reside within the FRET gate). The x-axis is concentration of N17Q35 seeds.
Figure 11:
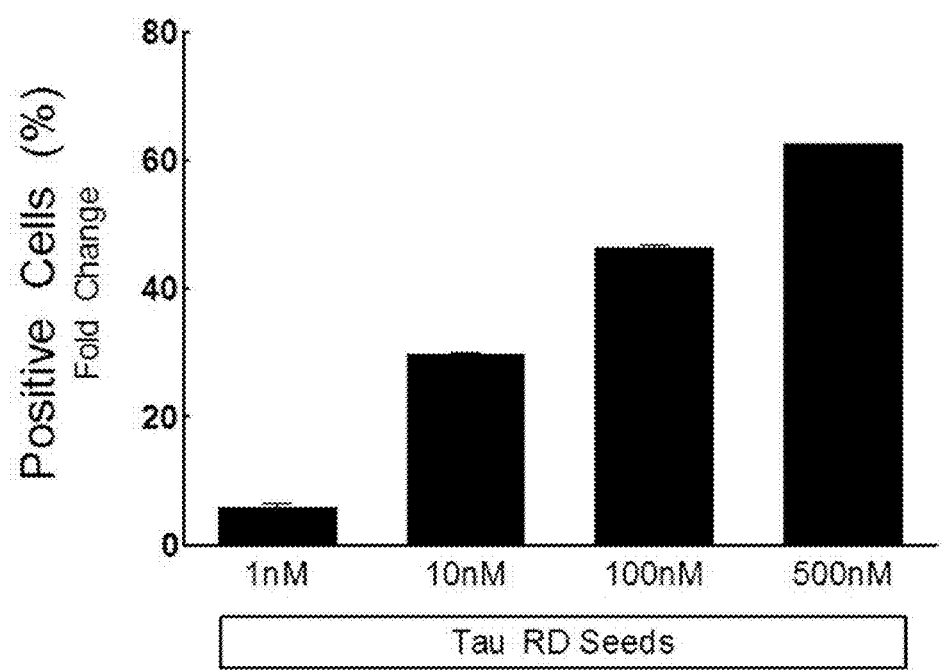
FIG. 11 depicts a graph showing the tau biosensor cell line (Tau RD ΔK expressing cells) can detect recombinant WT tau RD fibrils in a dose dependent manner. Experimental design was similar to that described in FIG. 10. Cells were harvested for flow cytometry and analyzed for FRET positivity. The y-axis is the fold change in percent positive cells (percent positive cells is the percentage of cells that reside within the FRET gate). The x-axis is concentration of Tau RD seeds.
Figure 12:
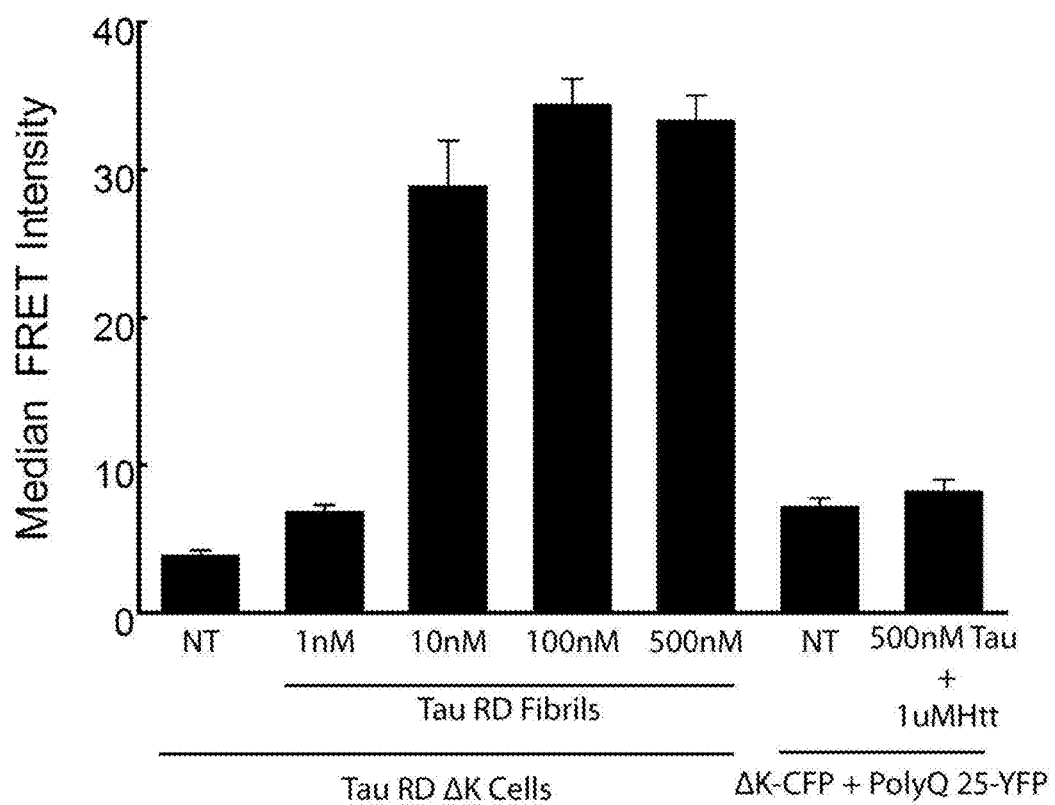
FIG. 12 depicts a graph showing the observed FRET response is specific and not due to an artifact of cell toxicity, fluorescence bleed through or other potential confounds. Theses data show that the FRET is homotypic and can only occur when both of the biosensor probes (i.e., the CFP and the YFP) are fused to the same protein type. For example, huntingtin aggregates and tau aggregates in a single cell are not co-localized to the same aggregate site. Rather, these two proteins form separate protein aggregate inclusions that are separated spatially within the cell compartment. Thus, no FRET should occur in this system. The first 5 bars in this graph show a dose response to tau RD fibrils, similar to the data shown in FIG. 11. For the last two bars in this graph, cells were co-transfected with tau RD ΔK CFP and PolyQ25 YFP. 24 hours later the cells were either sham treated (NT) or treated with both 500 nM tau RD fibrils and 1 uM huntingtin fibrils and analyzed by flow cytometry. The last two bars in this graph show that no change in FRET is observed in the treated cells relative to control cells. Thus, only homotypic aggregation can give rise to a FRET signal which is expected if the FRET signal is specific and not an artifact. The y-axis is median FRET intensity for the population that resides within the FRET gate.
Figure 13:
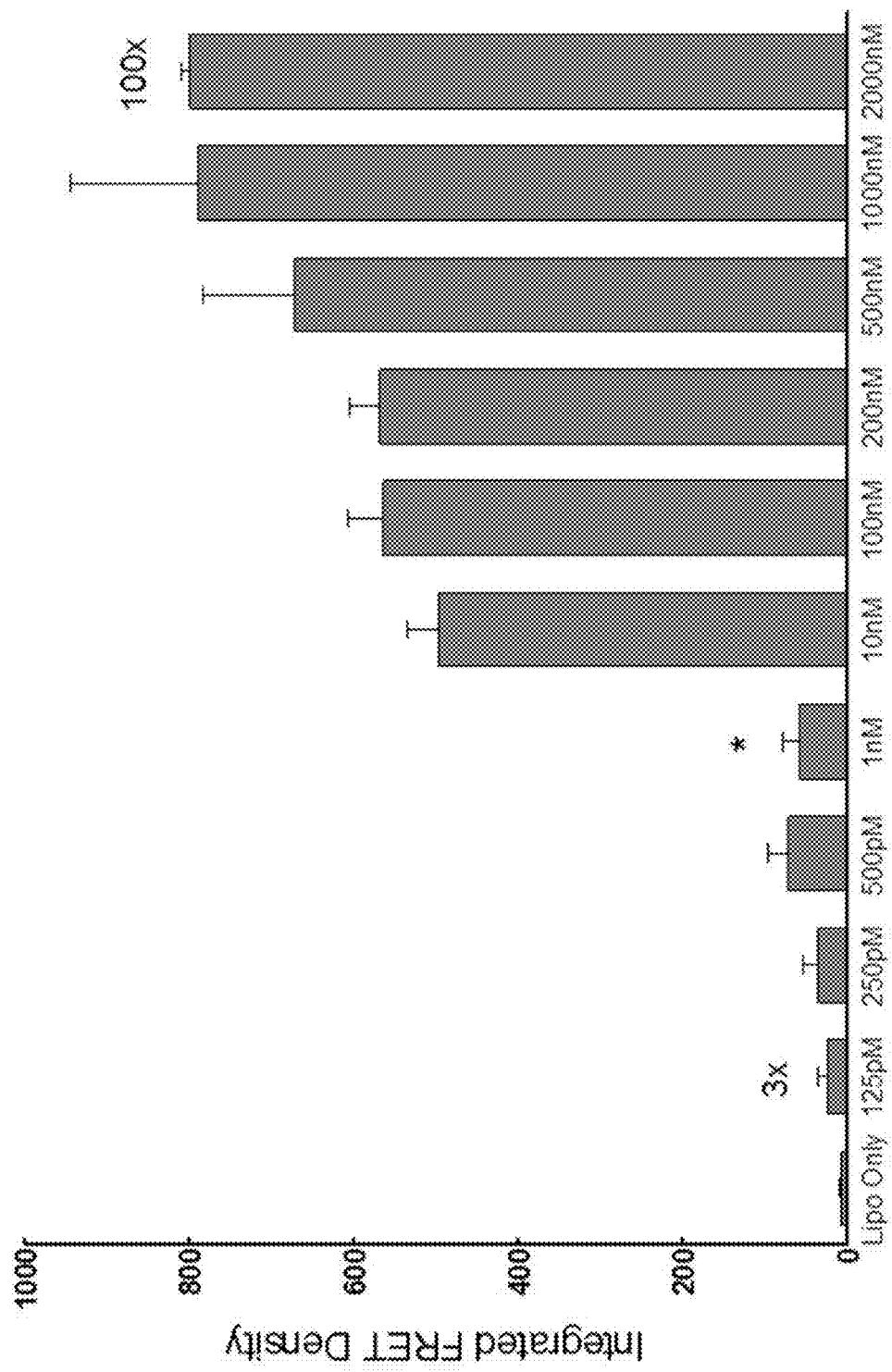
FIG. 13 shows a bar graph depicting the sensitivity and range of the biosensor cells when the detectable signal is measured by flow cytometry. HEK293 cells were transfected with tau RD P301S. Tau RD fibrils were applied to them for 24 hours at different doses. In transfected cells, a 3-fold response in FRET can be seen at 125 pM when FRET flow cytometry is used. The dynamic range of transfected cells spans ~100 fold above background. The y-axis is the fold change in integrated FRET density (integrated FRET density is the product of percent positive cells and median FRET intensity). The x-axis is tau fibril concentration (pM). Similar results can be obtained with a monoclonal stable cell line.

HEK293 cells are transiently transfected with $Htt_{Exon1}$ PolyQ25-CFP and $Htt_{Exon1}$ PolyQ25-YFP. 24 hours post transfection the cells are transduced with synthetic N17Q35 fibrils. 24 hours post transduction, the cells are harvested for flow cytometery and analyzed as discussed above. As demonstrated in FIG. 10, the huntingtin biosensor cell line can detect N17Q35 fibrils in a dose dependent manner. Similar results can be obtained with a monoclonal stable cell line.

Example 8. Synuclein Seeding Activity

Figure 19:
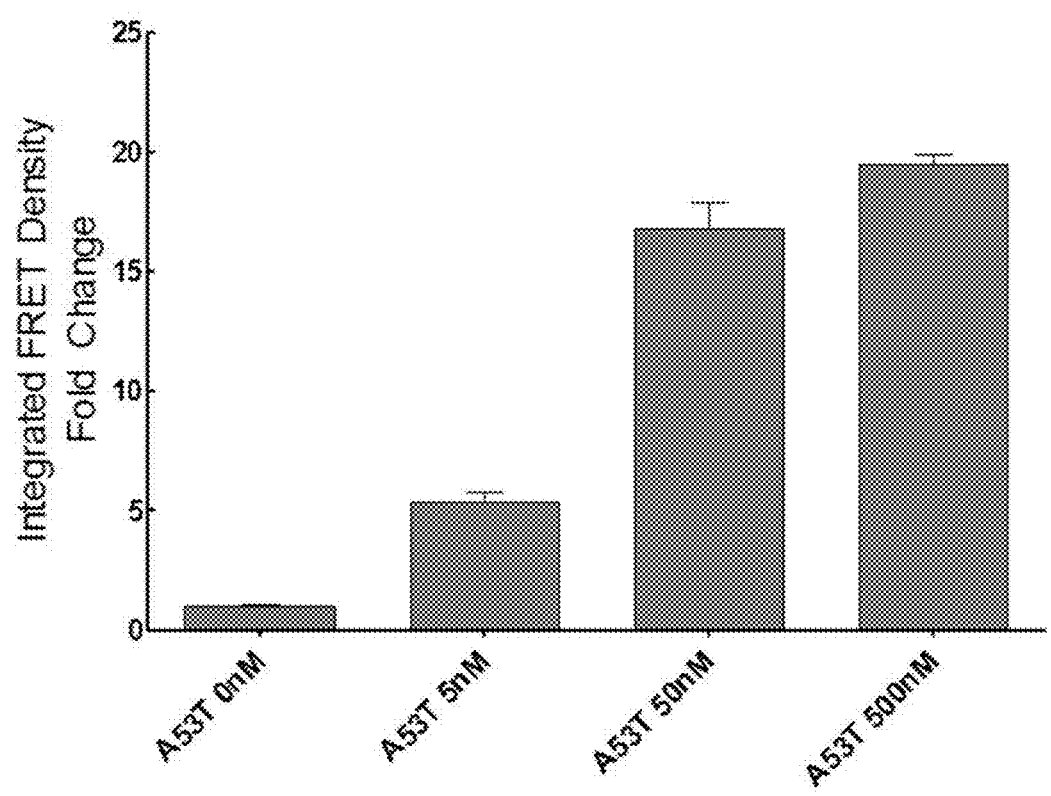
FIG. 19 depicts a graph showing the synuclein biosensor cell line can detect synuclein seeding in a dose dependent manner. Synuclein with the A53T mutation was transfected into cells (fused to CFP and YFP). 24 hours later, the cells were treated with recombinant wild type synuclein fibrils and harvested for flow cytometry. The y-axis is the fold change in percent positive cells (percent positive cells is the percentage of cells that reside within the FRET gate). The x-axis is concentration of N17Q35 seeds. Similar results can be obtained with a monoclonal stable cell line.

HEK293 cells are transiently transfected with synuclein with the A53T mutation fused to CFP and YFP. 24 hours later, the cells were treated with recombinant wild type synuclein fibrils and harvested for flow cytometry and analyzed as discussed above. As demonstrated in FIG. 19, the synuclein biosensor cell line can detect N17Q35 fibrils in a dose dependent manner. Recombinant or brain-derive synuclein seeds can be used. Similar results can be obtained with a monoclonal stable cell line. An α-synuclein A53T monoclonal line was established using the exact same protocol as described in Example 5.

What is claimed is:

1. A method for detecting one or more tau aggregates in a biological sample, the method comprising the steps of: (a) providing at least one mammalian cell comprising a first protein linked to a first reporter and a second protein linked to a second reporter, wherein the first protein and the second protein each comprise a similar aggregation-prone domain, such that the first protein and the second protein aggregate and produce a detectable signal; (b) contacting the at least one mammalian cell with a biological sample comprising a protein aggregate at a concentration equivalent to about 1 pM to about 100 nM of monomers, the protein aggregate comprising an aggregation-prone domain similar to the first and second protein, such that the protein aggregate is taken up by the cell; (c) measuring a fluorescence resonance energy transfer (FRET) signal by flow cytometry; and (d) comparing the amount of the detectable signal in the biological sample to the amount of a detectable signal produced by a control, wherein a change in the detectable signal indicates one or more protein aggregates are in the biological sample, wherein the mammalian cell is a HEK293T cell, the aggregation-prone domain of the first and second protein comprises a tau repeat domain with a P301S mutation, the first reporter is CFP and the second reporter is YFP.

2. The method of claim 1, wherein the biological sample is brain lysate.

3. The method of claim 1, further comprising an additional step before contacting the at least one mammalian cell with the biological sample, the additional step selected from the group consisting of (i) sonicating the biological sample, and (ii) a lipid-based transfection reagent.

4. The method of claim 2, wherein the biological sample is in contact with the at least one mammalian cell for at least 4 hours.

5. The method of claim 1, wherein the mammalian cell is a tau RD P301S monoclonal line ATCC CRL-3275.

* * * * *